US012788884B2

(12) United States Patent
Rollins et al.

(10) Patent No.: US 12,788,884 B2
(45) Date of Patent: Nov. 10, 2026

(54) FEEDBACK PREDICTIVE CONTROL APPROACH FOR PROCESSES WITH TIME DELAY IN THE MANIPULATED VARIABLE

(71) Applicant: Iowa State University Research Foundation, Inc., Ames, IA (US)

(72) Inventors: Derrick K. Rollins, Ames, IA (US); Yong Mei, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 399 days.

(21) Appl. No.: 18/519,204

(22) Filed: Nov. 27, 2023

(65) Prior Publication Data

US 2024/0091443 A1 Mar. 21, 2024

Related U.S. Application Data

(63) Continuation of application No. 17/447,242, filed on Sep. 9, 2021, now Pat. No. 11,850,399, which is a continuation of application No. 16/508,934, filed on Jul. 11, 2019, now Pat. No. 11,147,922.

(60) Provisional application No. 62/701,153, filed on Jul. 20, 2018, provisional application No. 62/697,798, filed on Jul. 13, 2018.

(51) Int. Cl.

| | |
|---|---|
| ***A61M 5/172*** | (2006.01) |
| ***A61M 5/142*** | (2006.01) |
| ***G16H 20/17*** | (2018.01) |

(52) U.S. Cl.

CPC ...... *A61M 5/1723* (2013.01); *A61M 5/14248* (2013.01); *G16H 20/17* (2018.01); *A61M 2205/3327* (2013.01); *A61M 2205/3334* (2013.01); *A61M 2205/3368* (2013.01); *A61M 2205/50* (2013.01); *A61M 2205/505* (2013.01); *A61M 2205/52* (2013.01); *A61M 2230/201* (2013.01); *A61M 2230/50* (2013.01); *A61M 2230/62* (2013.01); *A61M 2230/63* (2013.01)

(58) Field of Classification Search

None

See application file for complete search history.

(56) References Cited

U.S. PATENT DOCUMENTS

| | | | |
|---|---|---|---|
| 6,544,212 | B2 | 4/2003 | Galley et al. |
| 7,065,486 | B1 | 6/2006 | Thyssen |
| 8,273,052 | B2 | 9/2012 | Damiano et al. |

(Continued)

OTHER PUBLICATIONS

Rollins, Derrick, "Use of Input-based Models for Improved Glucose Control in Type 1 Diabetics," JDRF Funded Research, Project duration: Sep. 2010-Aug. 2012, Iowa State University, 2 pages.

(Continued)

*Primary Examiner* — Manuel A Mendez

(74) *Attorney, Agent, or Firm* — McKee, Voorhees & Sease, PLC

(57) ABSTRACT

This invention relates to a feedback predictive controller, systems comprising and methods employing the same. Preferably the feedback predictive controller and/or systems comprising the feedback predictive controller are part of an automatic insulin delivery system. The methods described herein can be used to control blood glucose concentration in a patient with diabetes. Preferably, the insulin delivery system is an artificial pancreas.

20 Claims, 22 Drawing Sheets

(56) References Cited

U.S. PATENT DOCUMENTS

| | | | | |
|---|---|---|---|---|
| 8,690,820 | B2 * | 4/2014 | Cinar | A61M 5/1723 600/319 |
| 9,597,453 | B2 | 3/2017 | Dobbles et al. | |
| 9,710,611 | B2 | 7/2017 | Booth et al. | |
| 11,147,922 | B2 | 10/2021 | Rollins et al. | |
| 2003/0130616 | A1 * | 7/2003 | Steil | A61B 5/1495 600/365 |
| 2010/0262117 | A1 | 10/2010 | Magni et al. | |
| 2011/0098548 | A1 | 4/2011 | Budiman et al. | |
| 2014/0066886 | A1 | 3/2014 | Roy | |
| 2015/0306314 | A1 * | 10/2015 | Doyle, III | A61M 5/1723 604/504 |
| 2016/0349044 | A1 | 12/2016 | Marell et al. | |
| 2018/0249345 | A1 | 8/2018 | Farkas et al. | |

OTHER PUBLICATIONS

Babb, Michael, "Pneumatic Instruments Gave Birth to Automatic Control", Control Engineering, pp. 20-24, Oct. 2, 1990.

Bahill, A. Terry, "A Simple Adaptive Smith-Predictor for Controlling Time-Delay Systems", Control Systems Magazine, pp. 16-22, 1983.

Bennett, Stuart, "The Past of PID Controllers", IFAC Digital Control: Past, Present and Future of PID Control, 11 pages, 2000.

Del Favero et al., "First Use of Model Predictive Control in Outpatient Wearable Artificial Pancreas", Diabetes Care, vol. 37, pp. 1212-1215, May 2014.

Doyle et al., "Glucose control strategies for treating type 1 diabetes mellitus, Journal of Process Control", vol. 17, pp. 571-594, 2007.

El-Khatib et al., "Bi-hormonal Closed-Loop Blood Glucose Control for Type 1 Diabetes", Sci Transl Med., vol. 2(27), 17 pages, Apr. 14, 2010.

Feng et al., "Performance Assessment of Model-Based Artificial Pancreas Control Systems", Prediction Methods for Blood Glucose Concentration, pp. 243-265, Nov. 2015.

Hovorka et al., "Overnight Closed-Loop Insulin Delivery in Young People With Type 1 Diabetes: A Free-Living, Randomized Clinical Trial", Diabetes Care, vol. 37, pp. 1204-1211, May 2014.

Jacobs et al., "Automated Control of an Adaptive Bihormonal, Dual-Sensor Artificial Pancreas and Evaluation During Inpatient Studies", IEEE Transactions on Biomedical Engineering, vol. 61, No. 10, pp. 2569-2581, Oct. 2014.

Kotz et al., "Multiple-Input Subject-Specific Modeling of Plasma Glucose Concentration for Feedforward Control", Ind. Eng. Chem Res., vol. 53, pp. 18216-18225, Nov. 3, 2014.

Kovatchev et al., "In Silico Preclinical Trials: A Proof of Concept in Closed-Loop Control of Type 1 Diabetes", Journal of Diabetes Science and Technology, vol. 3, Issue 1, pp. 44-55, Jan. 1999.

Kudva et al., "Closed-Loop Artificial Pancreas Systems: Physiological Input to Enhance Next-Generation Devices", Diabetes Care, vol. 37, pp. 1184-1190, May 2014.

Magni et al., "Biomedical Signal Processing and Control", Biomedical Signal Processing and Control, vol. 4, pp. 338-346, Apr. 15, 2009.

Magni et al., "Model Predictive Control of Type 1 Diabetes: An in Silico Trial", Journal of Diabetes Science and Technology, vol. 1, Issue 6, pp. 804-812, Nov. 2007.

Marchetti et al., "A Feedforward—Feedback Glucose Control Strategy for Type 1 Diabetes Mellitus", J Process Control, vol. 18(2), pp. 149-162, Feb. 2008.

Mehrafrooz et al., "PID Dead-Time Predictor Design for Industrial DCS Systems Using Smith Rule", International Conference on Intelligent and Advance Systems, pp. 1063-1068, 2007.

Rollins et al., "Optimal Deterministic Transfer Function Modelling in the Presence of Serially Correlated Noise", Chemical Engineering Research and Design, vol. 84(A1), pp. 9-21, Jan. 2006.

Rollins et al., "A New Feedback Predictive Control Approach for Processes with Time Delay in the Manipulated Variable", Chemical Engineering and Research and Design, https://doi.org/10.1016j.cherd.2018.06.018, 28 pages, Jun. 14, 2018.

Rollins et al., "An Extended Static and Dynamic Feedback—Feedforward Control Algorithm for Insulin Delivery in the Control of Blood Glucose Level", Ind. Eng. Chem. Res., vol. 54, pp. 6734-6748, Jun. 10, 2015.

Rollins et al., "Block-oriented feedforward control with demonstration to nonlinear parameterized Wiener modeling", Chemical Engineering Research and Design, vol. 109, pp. 397-404, Feb. 20, 2016.

Rollins et al., "Dynamic Modeling With Correlated Inputs: Theory, Method, and Experimental Demonstration", Ind. Eng. Chem. Res., vol. 54, pp. 2136-2144, Feb. 3, 2015.

Rollins et al., "The Development of a Virtual Sensor in Glucose Monitoring for Non-Insulin Dependent People", Bioinformatics and Diabetes, vol. 1, Issue 1, pp. 19-36, May 10, 2014.

Rollins et al., "Free-living inferential modeling of blood glucose level using only noninvasive inputs", Journal of Process Control, vol. 20, pp. 95-107, 2010.

Setz et al., "Application of Model Predictive Control to a Cascade of River Power Plants", Proceedings of the 17th World Congress, The International Federation of Automatic Control in Seoul, Korea, 6 pages, Jul. 6, 2008.

Thabit et al., "Home Use of an Artificial Beta Cell in Type 1 Diabetes", The New England Journal of Medicine, pp. 2129-2140, Nov. 26, 2015.

Ziegler et al., "Optimum Settings for Automatic Controllers", Transactions of the A.S.M.E., pp. 759-765, Nov. 1942.

Bodymedia, "SenseWear" User Manual, Version 8, 28 pages, 2014.

Ding et al., "Sensor Monitoring of Physical Activity to Improve Glucose Management in Diabetic Patients: A Review", Sensors, vol. 16, 13 pages, 2016.

Polar, "RS800CX", User Manual, 68 pages, Aug. 4, 2016.

Schaepelynck et al., "Advances in pump technology: insulin patch pumps, combined pumps and glucose sensors, and implanted pumps", Diabetes & Metabolism, vol. 37, pp. S85-S93, 2011.

Turksoy et al., "An Integrated Multivariable Artificial Pancreas Control System", Journal of Diabetes Science and Technology, vol. 8(3), pp. 498-507, 2014.

* cited by examiner

FEEDBACK PREDICTIVE CONTROL APPROACH FOR PROCESSES WITH TIME DELAY IN THE MANIPULATED VARIABLE

CROSS REFERENCE TO RELATED APPLICATION

This is a continuation application of U.S. Ser. No. 17/447,242, filed Sep. 9, 2021 now U.S. Pat. No. 11,850,399, issued Dec. 26, 2023, which is a continuation of U.S. Ser. No. 16/508,934, filed Jul. 11, 2019 (now U.S. Pat. No. 11,147,922, issued Oct. 19, 2021), which claims priority under 35 U.S.C. § 119 to Provisional Application U.S. Ser. No. 62/697,798, filed on Jul. 13, 2018 and Provisional Application U.S. Ser. No. 62/701,153 filed on Jul. 20, 2018, all of which are herein incorporated by reference in their entirety including without limitation, the specification, claims, and abstract, as well as any figures, tables, or examples thereof.

TECHNICAL FIELD

This invention relates generally to a control system that utilizes feedback predictive control. More specifically, but not exclusively, the invention relates to an automatic insulin delivery system that employs feedback predictive control.

BACKGROUND OF THE INVENTION

In a person without diabetes, several systems including, for example, the metabolic, endocrine, and cardiovascular systems, function collectively to maintain homeostasis. However, in a person with diabetes, the inherent glucose regulation mechanism is dysfunctional. Glucose levels are affected by the state of the metabolic-physiological-endocrine system and disturbances to that system. Disturbances such as stress, physical activity, hormonal changes, periods of growth, medications, illness/infection and fatigue, that are unknown in many cases, can cause large changes in blood glucose concentration (BGC) for individuals with type 1 diabetes. Their combined effects on BGC are highly complex, highly correlated, and difficult to measure and model accurately. In a normal person, several systems, such as the metabolic, endocrine, and cardiovascular systems function collectively to maintain homeostasis. However, in a person with diabetes their inherent glucose regulation mechanism becomes dysfunctional. If the amount of carbohydrates in a meal was the only variable to affect BGC, management would be much simpler. However, not only are there other disturbances in food, such as fats and proteins, but also in the levels and types of activities as well as physical and emotional stress, among many others. Furthermore, not only does BGC change due to several disturbances, their impact on glucose level is highly correlated, dynamic, and nonlinear, making it difficult to distinguish the effect each input has on BGC.

Insulin therapy involves multiple daily doses of insulin before meals to correct high blood glucose, with the amount either pre-recommended by a physician or decided by the patient on the basis measured BGC and the number of carbohydrates they estimate will be ingested at the time of the meal. This protocol is inconvenient and unreliable. It often results in hypoglycemic and hyperglycemic episodes, both of which can be life-limiting and life-threatening. Thus, there has been a desire to develop more optimized insulin delivery systems and protocols. This has included research to develop automatic insulin delivery systems.

The potential for successful automatic insulin delivery has entered a new era due to recent technological advancements of insulin pumps and blood glucose sensors. Consequently, for full automation and control capable of reducing the variance in BGC, the control algorithm must be capable of tight control for major disturbances such as meals, activity, and stress. However, the control systems in place to date are not sufficient to address the complexities of BGC control.

For example, classical time-delayed feedback control (FBC) approaches, such as the Smith Predictor, address time delay (θ) in the controlled variable (CV) when a change in the manipulated variable (MV) affects CV immediately but the measurement of CV corresponding to the MV change is much later (i.e., delayed). In contrast, when MV has time delay, a change in MV does not affect CV until θ time later. Thus, in this case, optimal feedback control requires knowledge of the value(s) of CV after it begins to change from the current change in MV, i.e., future predictions of CV a time distant into the future at least as great as θ. Hence, an optimal FBC-type of algorithm for addressing dead time in MV requires future prediction of CV to change MV. The classical FBC-type of algorithm for dead time in MV is model predictive control (MPC). The MPC control law is for the future predicted value of CV to be at the set point an integer value of sampling time steps (J) beyond the amount of dead time. Hence, the effectiveness of MPC depends strongly on the accuracy of the future prediction of CV, which decreases as J increases. Moreover, the larger the time lag for MV, the longer it takes to reach the set point and the greater J will be. Thus, if time lag for MV is significant, the more difficult it will be to predict CV and the greater the potential error there will be in that prediction. For this reason, all types of classical time-delay feedback control algorithms are unable to address the complexities of BGC.

Theoretically, the superiority of feedforward control (FFC) over all other control systems is that corrective action can be taken to cancel the effects of disturbances on the control variable (i.e., BGC) proactively. Currently, FFC is not capable of approaching this theoretical limit, i.e., very tight control of BGC, because insulin, the MV, can only decrease BGC. Before it is possible to approach this idealized control, a new hormone needs to be developed and approved by the FDA that can increase BGC. In addition, FFC has not been capable of addressing the complexity of various measured disturbances impacting the regulation of blood glucose levels associated with diabetes due to the limits of sensor technology as was as effective model development of the complex causative relationships of disturbances and the controlled variable. These insufficiencies will have to be overcome before FFC is able to significantly improve control of BGC. Thus, feedforward control, while being theoretically superior, is at this time, incapable of serving as an approved automatic insulin delivery system.

Consequently, there is a need for a system providing automatic delivery of insulin with minimal variability around the desired BGC target using a predictive feedback control approach. More specifically, currently, the most practical challenge is providing an effective FBC-type of predictive control system in the presence of unmeasured disturbances, with a minimal prediction horizon (i.e., prediction a distance θ into the future) for the greatest possible prediction accuracy of CV, which leads to the most effective control system possible for BGC.

Accordingly, it is an objective of the claimed invention to provide an methodology that more accurately controls blood glucose levels for FBC-type predictive control systems.

Other objects, advantages and features of the present invention will become apparent from the following specification taken in conjunction with the accompanying figures.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

Figure 1A:
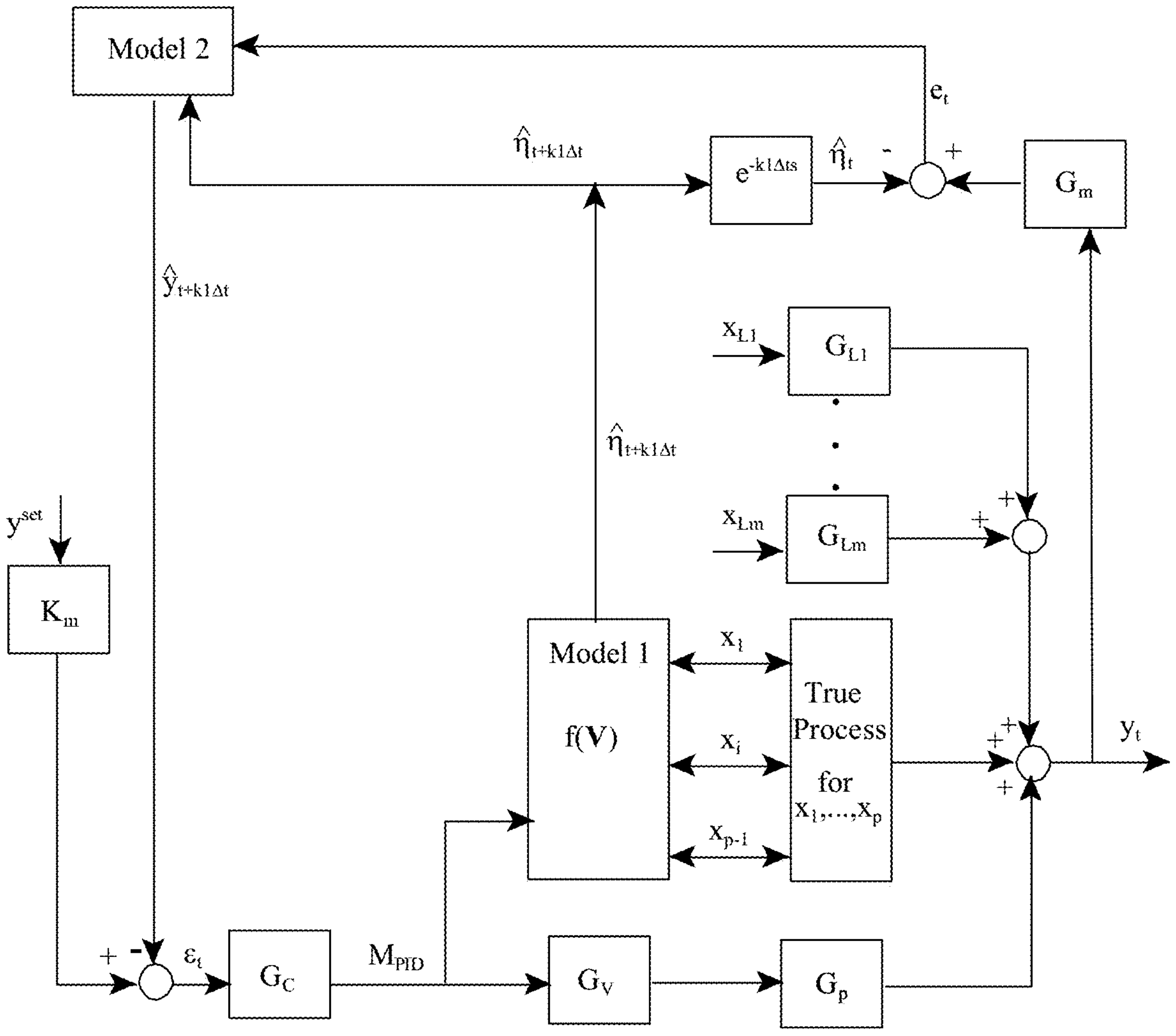
FIG. 1A is an exemplary block diagram for a feedback predictive controller (FBPC) employing a traditional controller such as a PID controller.

Various embodiments of the present invention are described in detail with reference to the figures. The reference to various embodiments does not limit the scope of the invention. Figures represented herein are not limitations to the various embodiments according to the invention and are presented for exemplary illustration of the invention.

DETAILED DESCRIPTION

The embodiments of this invention are not limited to particular insulin pumps, apparatuses for monitoring insulin and/or blood glucose levels, activity inputs, and stress measuring devices. Moreover, while the Feedback Predictive Controller and systems employing the same are primarily discussed in the context of diabetes and BGC control, the controller is not limited to diabetes and BGC control. Rather it is suitable for other systems, particularly, those having significant lag time. It is further to be understood that all terminology used herein is for the purpose of describing particular embodiments only and is not intended to be limiting in any manner or scope. For example, all units, prefixes, and symbols may be denoted in its SI accepted form.

Numeric ranges recited within the specification are inclusive of the numbers defining the range and include each integer, fraction, and decimal within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range such as 1, 2, 3, 4, 5, and 6, fractions such as 1¾, 3⅓, and 4⅝, and decimals such as 2.3, 4.1, and 5.7. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Definitions

As used herein the singular forms "a," "an" and "the" can include plural referents unless the content clearly indicates otherwise.

As used herein the term "BGC" refers to blood glucose concentration. It is not limited to any particular measurement unit.

As used herein the term "FBC" refers to feedback control or any synonyms thereof, including for example, "feed-back control."

As used herein the term "FBE" refers to feedback error or any synonyms thereof and is the deviation of the controlled variable from its set point value.

As used herein the term "FBPC" refers to a feedback predictive control or feedback predictive controller as described in greater detail herein.

As used herein the term "MPC" refers to model predictive control.

As used herein the term "dead time" refers to the amount of time it takes for the controlled variable to start to respond after a change in the manipulated variable.

As used herein the term "lag" refers to a variable not reaching its final value immediately when the variable begins to change due a change in another variable causing it to change. A variable without lag reaches its final value immediately.

As used herein the term "prediction horizon" refers to the distance into the future that the value of the controlled variable must be estimated.

As used herein the term "controlled variable" refers to the output the control system, the purpose of the control system is to keep the controlled variable at the set point.

As used herein the term "manipulated variable" refers to the input variable that is adjusted to keep the controlled variable in the system at a set point.

As used herein the term "PID controller" refers a proportional-integral-derivative controller used in control systems that require continuously modulated control.

Feedback Predictive Controller

The systems and methods described herein comprise a feedback predictive controller ("FBPC"). Preferably, the FBPC is a model-based feedback predictive control system that uses a predictive feedback error (deviation from set point) to provide changes to the system in an effort to nullify the deviation. Surprisingly it has been found that by employing a feedback controller with a predicted FBE, one can reduce, or preferably minimize, deviation of the controlled variable from its set point in cases where manipulated variables have large dead time and time lag. In an aspect of the invention, the set point of a controlled variable is set by the user of the control system. Thus, the set point is determined by the user of the control system.

In the context of BGC and diabetes, accurate modeling of BGC 30 to 60 minutes into the future is critical for model-based feedback predictive control strategies that use the predictive feedback error (deviation from set point) since it takes 30 to 60 minutes for current changes in insulin flow rate to change BGC. To achieve accurate modeling (i.e., estimation) of the future value of the control variable is essential. Preferably, the models will not drift over time, have minimal bias, and provide at least 70%, 75%, 80%, 85%, 90%, 91%, 92%, 93%, 94%, 95%, 96%, 97%, 98%, or 99% accuracy and fit over at least 24 hours, 36 hours, 48 hours, 3 days, 4, days, 5 days, 6 days, 7 days, 2 weeks, 3 weeks, or one month.

The FBPC system preferably comprises a two-stage method that first applies the Wiener/Semi-Coupled method and obtains the input-only Model 1. It then uses the pre-whitening method to model the serial correlation structure of the Model 1 residuals to address unmeasured disturbances and model bias. This is Model 2 and is the predictive model for future BGC using current and past BGC measurements. According to this system, BGC is predicted a distance into the future equal to the given value of dead time for exogenous insulin flow rate. The future feedback error is determined using this value and a conventional PID controller is used to manipulate insulin flowrate in the present. Preferably, FBPC control uses a PID control algorithm, with the minimum prediction horizon, no specified control horizon, and an inherent cause-and-effect relationship between MV and CV that is "built-in" to the PID structure.

The FBPC and systems and methods employing the same have provide improvements and advantages over existing controllers, systems and methods for controlling BGC. For example, one such advantage is that it does not require a cause-and-effect model for the relationship of insulin flow rate on BGC. This is significant as a cause-and-effect model is very difficult to accurately obtain in real-life. Model-based predictive control algorithms such as FFC and MPC require accurate cause-and-effect modeled relationship of insulin flow rate on BGC, a critical limitation of such approaches.

According to the invention as described herein FBPC is similar to MPC in certain respects; however, MPC uses an FBE that is greater than a distance θ into the future (i.e., a greater prediction horizon). Therefore, in applications where the accuracy of CV declines as the prediction horizon increases, which is common, MPC could perform much worse than FBPC when its prediction horizon is significantly greater than θ. In addition, there are other fundamental differences in these two control algorithms that can result in significantly different control performance. MPC uses a fitted mathematical model for the manipulated variable and FBPC uses a form of the PID control algorithm. Thus, MPC performance depends on the accuracy of this model, which can be difficult to obtain in many applications. Furthermore, MPC has one discrete tuning parameter. Therefore, the one-dimensional tuning space of MPC has the advantage of simplicity over the possible three-dimensional one of FBPC. This is also a disadvantage in many applications. FBPC has a tuning space as large as three-dimensions and thus, more geometric directions for finding optimal tuning parameters. In addition, its tuning parameters are continuous and can be set to any value in a range, whereas the one for MPC can only be set at discrete values, in increments that depend on the sampling rate. Furthermore, the prediction horizon for MPC depends on the dynamic lag of MV. The larger this lag, the greater the prediction horizon, and hence the worse prediction accuracy can be. Since the prediction horizon for FBPC is fixed at θ distance in the future, process lag does not affect its prediction horizon.

In a general class, MPC can be any type of control system that uses a model for the control horizon and a model for the prediction horizon. However, as described above, the model for the control horizon must have an accurate cause-and-effect relationship between the inputs, especially MV, and the output, CV. This is usually very difficult to achieve in practice and required by all MPC type of control algorithms. Hence, a critical advantage of FBPC is that it does not use a control horizon and thus, does not need, or use, a model horizon to make changes in MV.

Figure 1B:
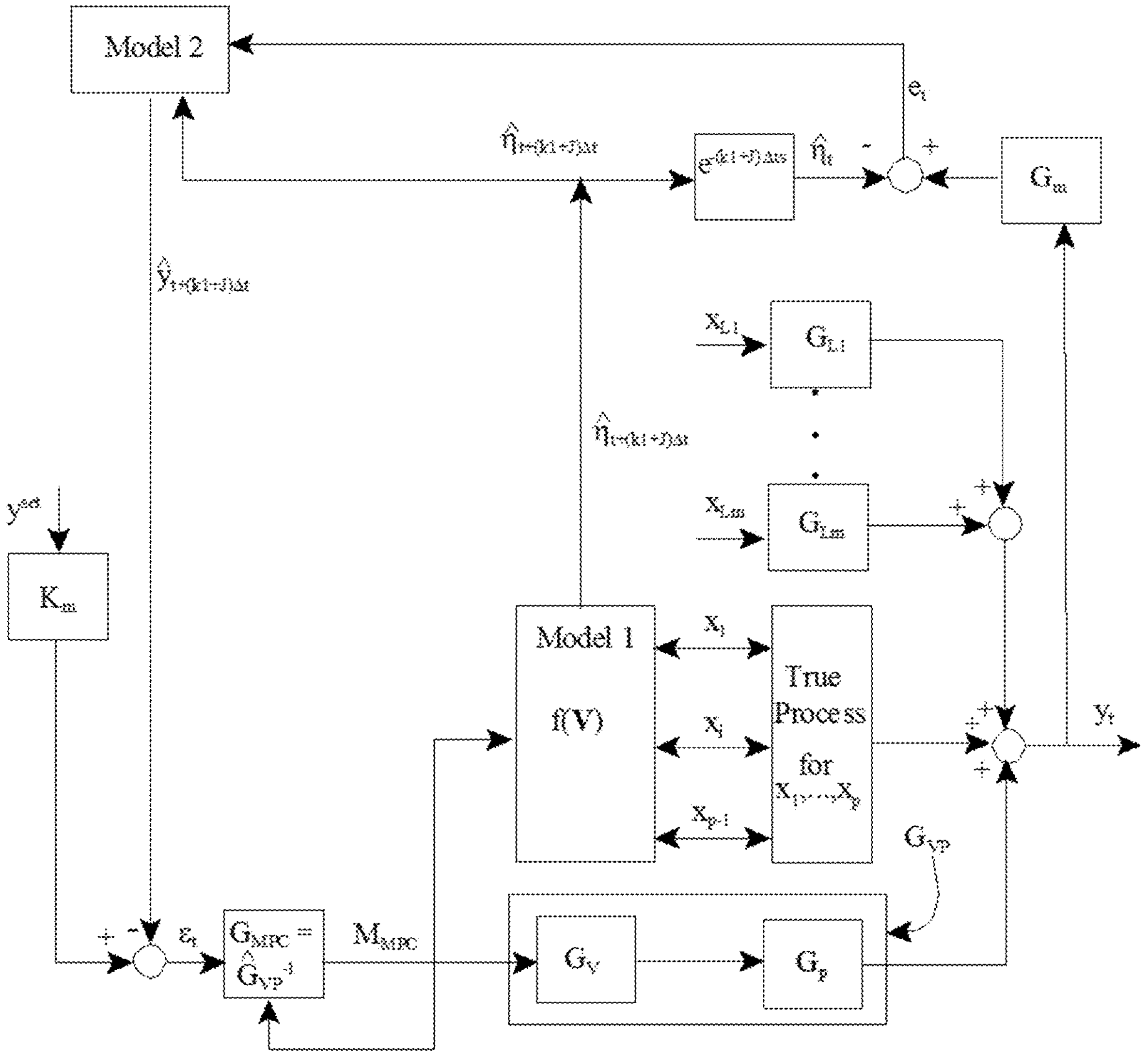
FIG. 1B is an exemplary block diagram for a feedback predictive controller (FBPC) where employing a model predictive controller.

An exemplary block diagram for FBPC is shown in FIG. 1A. The controller $G_c$ is preferably a PID controller. FIG. 1B provides an exemplary block diagram mimicking FIG. 1A, but employing a model predictive controller. In both FIGS. 1A and 1B, the output from $G_v$ represents adjustments of the MV. In an automatic insulin delivery system, the output from $G_v$ would represent varying the insulin flow rate or quantity of insulin administered to a patient.

Figure 3A:
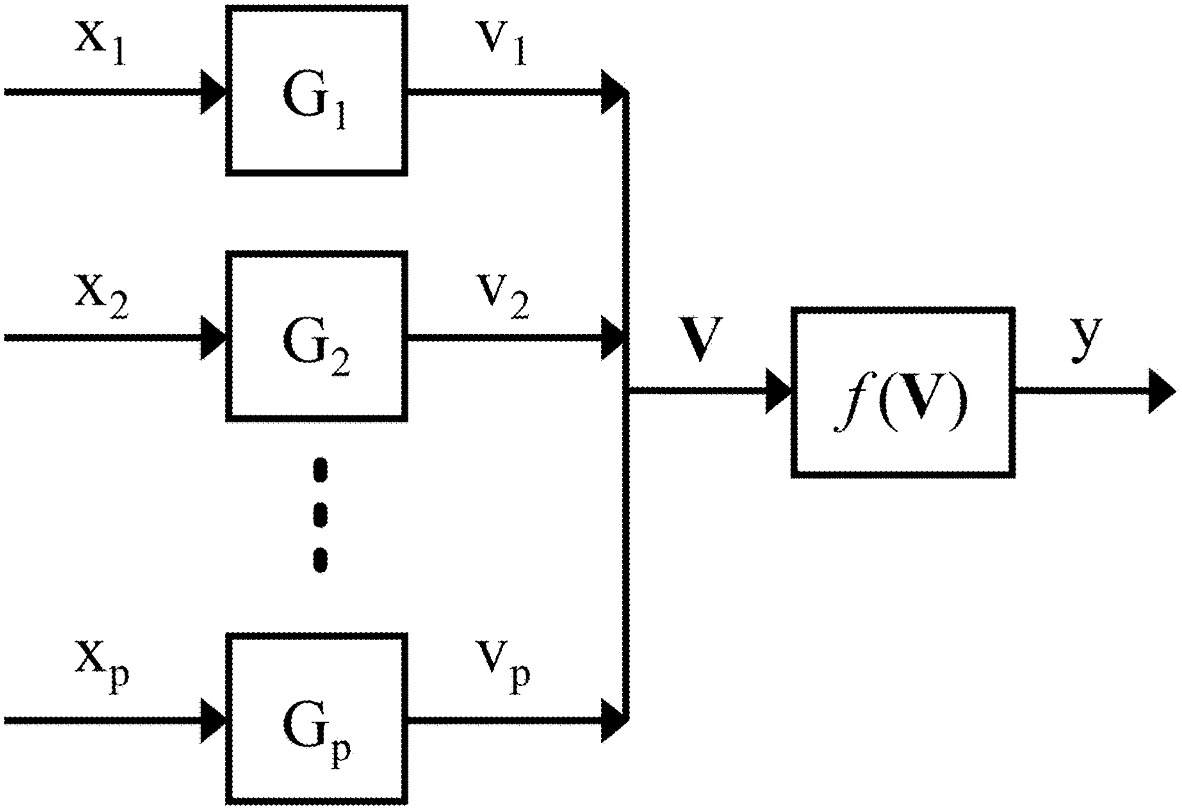
FIG. 3A shows a block diagram of a traditional Wiener model.

According to an aspect of the invention, Model 1 can apply a Wiener model or a Wiener/Semi-Coupled model. A traditional Wiener model is shown in FIG. 3A. Preferred Wiener/Semi-Coupled models include those shown in FIGS. 3B and 3C. In the Wiener model (FIG. 3A), the inputs are represented by $x_i$ where I=1, . . . , p, which are the measured noninvasive variables or disturbances. Each input has its own linear dynamic block, $G_i$, and each dynamic block has an intermediate, unobservable output, $v_i$, which represents the independent dynamic response of its corresponding input. All the intermediate $v_i$'s are collected and passed through an unrestricted static gain block, $f(V)$, to produce the final output, y, which represents BGC. If employed in BGC control system, $x_i$ represents things like food, activity, and stress, i.e., disturbances that affect BGC and the output variable y is BGC.

Figure 3B:
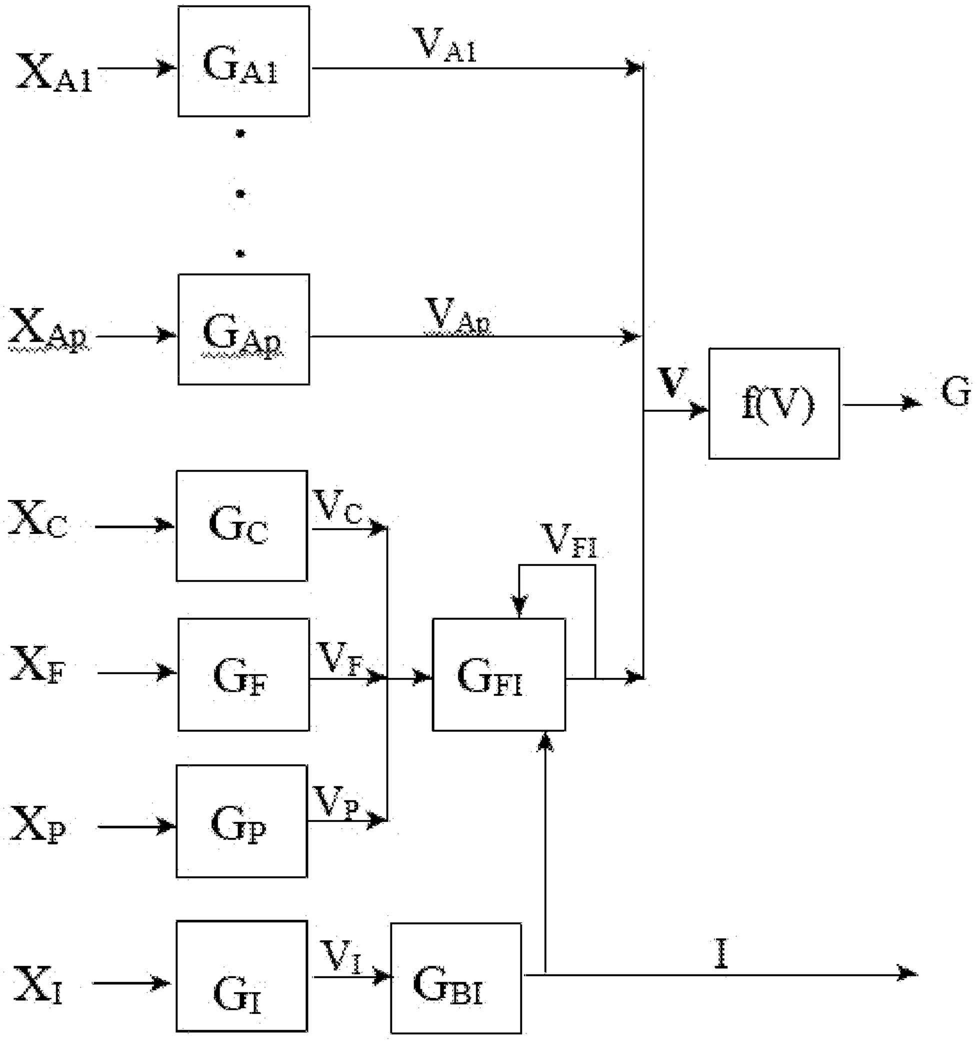
FIG. 3B shows a block diagram of a Wiener/Semi-Coupled model.
Figure 3C:
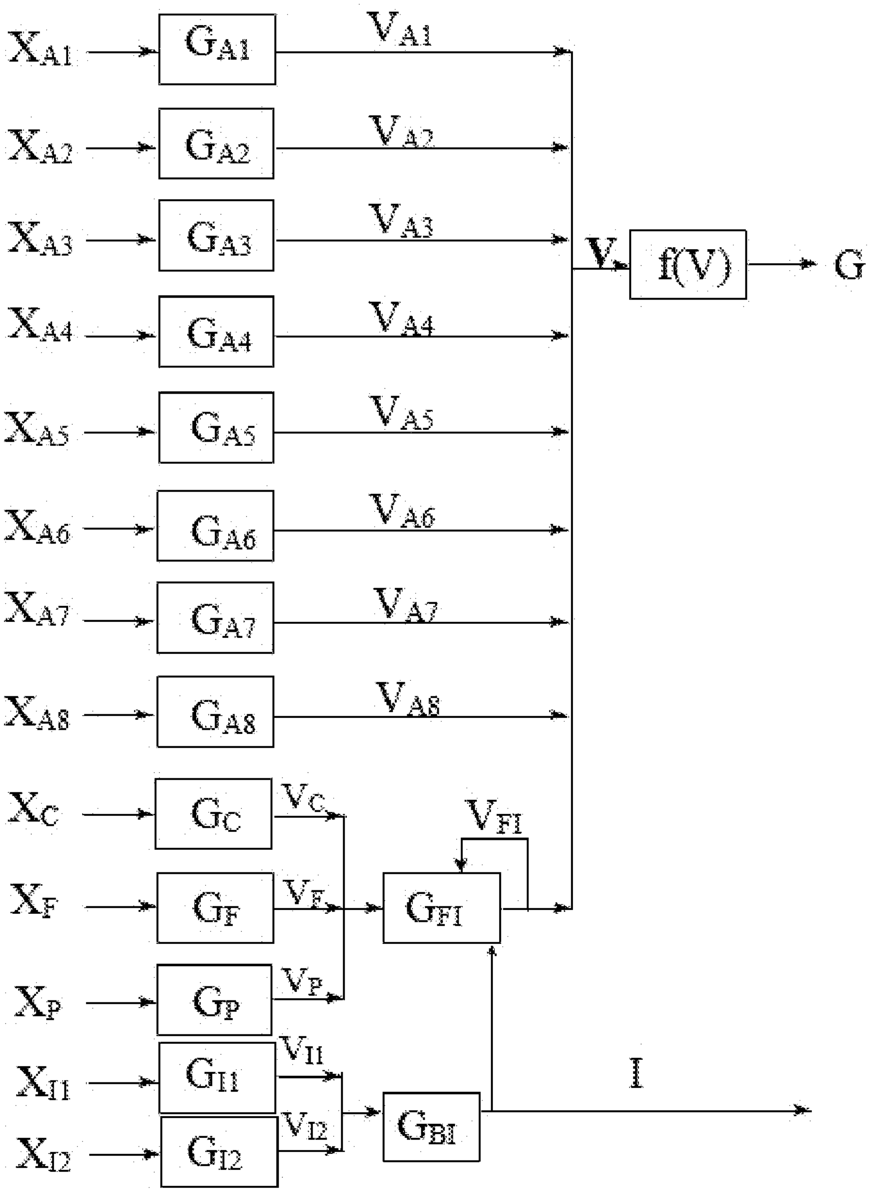
FIG. 3C shows a block diagram of a Wiener/Semi-Coupled model with thirteen specific inputs for disturbances on the system.

As shown in FIGS. 3B and 3C, all of the inputs, $x_i$, pass through a linear dynamic block to produce the unobservable dynamic output variables $v_i$. Note that, $I=A_1, \ldots, A_p$, for p activity inputs, C for carbohydrates, F for fats, P for proteins, and I for blood insulin concentration (BIC). FIG. 3C shows an exemplary semi-coupled network 14 accounting for thirteen inputs 16 (disturbances). This includes two insulin inputs, three consumed energy inputs, and eight activity inputs.

In FIGS. 3A-3C, "Y" represents BGC; "$Y^{set}$" denotes the set point for BGC, i.e., the desired value at θ; "$x_{a1}$" to "$x_{I2}$" represent measured input variables (e.g. physical activities, insulin, and meal logs); all "v's" are dynamic effects of corresponding "x" inputs; "$G_{BI}$" represents the BGC due to insulin only; "$G_{FI}$" represents the BGC due to food and insulin only; "$G_1$" to "$G_p$" represent dynamic block for each input; "$V_{FI}$" provides feedback to $G_{FI}$ block of the BGC due to food and insulin changes only.

Consumed Energy

There are three main categories of consumed energy: carbohydrates, fats, and proteins. As shown in FIGS. 3A and 3B, these are accounted for by $X_C$, $X_F$, and $X_P$. The consumed energy outputs feed into the $G_{FI}$ block along with the output from the $G_{BI}$ block. The output from the $G_{FI}$ block then combines with the activity disturbances.

Insulin

There are two types of insulin: basal and bolus. Basal insulin, often referred to as background insulin, functions to keep blood glucose levels consistent during periods of fasting. Basal insulin is produced by the pancreas. Basal insulin can also be provided by the continuous administration of fast-acting insulin in small doses. Bolus insulin is faster acting insulin provided in some dosage. It can be administered intravenously, by intramuscular injection, by intrathecal injection, or by subcutaneous injection. In FIGS. 3B-3C, these are accounted for by $X_I$, in particular, $X_{I1}$ and $X_{I2}$. As shown in FIGS. 3B-3C, the insulin inputs combine to form the $G_{BI}$ block, which feeds into the $G_{FI}$ block. Preferably, the $G_{FI}$ block also contains the output from the consumed energy inputs.

Activities

There are many activities that affect BGC. These activities include, but are not limited to, exercise, walking, working, and casual movement. These activities can be monitored by monitoring and/or measuring body position, movement, heat dissipated, skin temperature, near body temperature, galvanic skin response, and sleep, etc. In order to monitor body position and movement, it is preferable to use a two-axis accelerometer. Sleep can be monitored by the lack of certain kinds of movement. The heat dissipated from the body can be accounted for based on the body's heat flux. Skin temperature and near-body temperature can be measured by sensitive thermistors. Galvanic skin response (GSR) can be measured by the conductivity of a person's skin as it varies due to physical and emotional stimuli.

Any type and number of monitoring systems can be used to monitor the various activities. In a preferred embodiment, a single monitoring system is employed to monitor all activities at once. A preferred monitoring system is a type similar to the SenseWear® Pro3 Body Monitoring System, previously available from BodyMedia, Inc. in Pittsburgh, Pennsylvania.

Feedback Predictive Control Model

The dynamic blocks for the inputs have second-order-plus-dead-time-plus-lead (SOPDTPL) form as shown in Eq. 1 below:

$$\tau_i^2\frac{d^2v_i(t)}{dt^2}+2\tau_i\zeta_i\frac{dv_i(t)}{dt}+v_i(t)=\tau_{ai}\frac{dx_i(t-\theta)}{dt}+x_i(t-\theta_i) \tag{1}$$

where $\tau_i$ is the time constant, $\zeta_i$ is the damping coefficient, $\tau_{ai}$ is the lead parameter and $\theta_i$ is the dead time. Using a backward difference approximation $$\left(\text{e.g., } \frac{dv_1(t)}{dt}\approx\frac{v_{1,t}-v_{1,t-\Delta t}}{\Delta t}\right)$$

applied to a sampling interval of Δt, an approximate discrete-time form of Eq. 1 is:

$$v_{i,t}=\delta_{1,i}v_{i,t-\Delta t}+\delta_{2,i}v_{i,t-2\Delta t}+\omega_{1,i}x_{i,t-k_i\Delta t}+\omega_{2,i}x_{i,t-(k_i+1)\Delta t} \tag{2}$$

where $\omega_{2,i}=1-\delta_{1,i}-\delta_{2,i}-\omega_{1,i}$ to satisfy the unity gain constraint with $$\delta_{1,i}=\frac{2\tau_i^2+2\tau_i\zeta_i\Delta t}{\tau_i^2+2\tau_i\zeta_i\Delta t+\Delta t^2} \tag{3}$$

$$\delta_{2,i}=\frac{-\tau_i^2}{\tau_i^2+2\tau_i\zeta_i\Delta t+\Delta t^2} \tag{4}$$

$$\omega_{1,i}=\frac{(\tau_{ai}+\Delta t)\Delta t}{\tau_i^2+2\tau_i\zeta_i\Delta t+\Delta t^2} \tag{5}$$

A dynamic mass balance on $G_{FI}$ block in FIGS. 3A-3C, which represents the BGC due to food and insulin only, gives $$\frac{dV_{FI}(t)}{dt}=a_Cv_C(t)=a_Fv_F(t)+a_Pv_P(t)-a_{FI}I(t)V_{FI}(t) \tag{6}$$

where $a_C$, $a_F$, $a_P$, and $a_{FI}$, are estimated model parameters; I(t) is the unmeasured blood-insulin concentration (BIC) at time t; and $V_{FI}(t)$ is the BGC due to food and insulin changes only. Similarly, a dynamic mass balance on the GBI block, which represents BIC, gives $$\frac{dI(t)}{dt}=a_Iv_I(t)-a_{BI}I(t) \tag{7}$$

where $a_I$ and $a_{BI}$, are estimated model parameters. The function $f(V)$ is called "the static function." This function can theoretically be of any form. For effectiveness under mild extrapolation, in modeling real BGC data we will use a first-order linear regression structure, given in discrete form as:

$$f(V)=\eta_t+\varepsilon_t=a_0+V_{FI,t}+a_{A1}v_{A_1j}+\ldots+a_{Ap}v_{A_p,t} \tag{8}$$

where $a_0$ and $a_{Ai}$'s are static estimated model parameters.

Preferably, the FBPC controller models unmeasured disturbances and bias in Model 2. Specifically, a noise model structure is applied to Eq. 8 as follows:

$$y_t = \eta_t + N_t, \tag{9}$$

where $$N_t = \frac{\theta_q(B)}{\phi_p(B)} a_t = \tag{10a}$$

$$\frac{1 - \theta_1 B - \theta_2 B^2 - \ldots - \theta_q B^q}{1 - \phi_1 B - \phi_2 B^2 - \ldots - \phi_p B^p} a_t = \frac{a_t}{\Phi(B)} = \frac{a_t}{\left[1 - \varphi_1 B - \varphi_2 B^2 - \ldots\right]} \forall\, t$$

$$\text{subject to } \sum \varphi_1 - 1 \tag{10b}$$

with $$a_t \overset{indep}{\sim} N(0, \sigma^2) \tag{11}$$

such that $y_t$ is the measured BGC at t and $B^{\gamma} x_t = x_{t-\gamma\Delta t}$. Eq. 10b is a critical innovation of this work as it eliminates model bias, i.e., model drift of the CV over time. Then from substituting Eq. 10 into Eq. 9 and rearranging gives:

$$y_t \lfloor 1 - \varphi_1 B - \varphi_2 B^2 - \ldots \rfloor = \eta_t \lfloor 1 - \varphi_1 B - \varphi_2 B^2 - \ldots \rfloor + a_t \tag{12}$$

With dead time θ=kΔt, Eq. 12 is $$y_t \lfloor 1 - \varphi_1 B^k - \varphi_2 B^{k+1} - \ldots \rfloor = \eta_t \lfloor 1 - \varphi_1 B^k - \varphi_2 B^{k+1} - \ldots \rfloor + a_t \tag{13}$$

$$\Rightarrow y_t = \eta_t + \varphi_1 (y_{t-k\Delta t} - \eta_{t-k\Delta t}) + \varphi_2 (y_{t-(k+1)\Delta t} - \eta_{t-(k+1)\Delta t}) + \ldots + a_t \tag{14}$$

Modification of Eq. 14 for predicting θ=kΔt time steps into the future gives $$\begin{aligned} \hat{y}_{i+k\Delta t} &= \hat{\eta}_{t+k\Delta t} + \hat{\varphi}_1 (y_t - \hat{\eta}_t) + \hat{\varphi}_2 (\hat{y}_{t-\Delta t} - \hat{\eta}_{t-\Delta t}) + \ldots \\ &= \hat{\eta}_{t+k\Delta t} + \hat{\varphi}_1 e_t + \hat{\varphi}_2 e_{t-\Delta t} + \ldots \end{aligned} \tag{15}$$

where "^" is used for estimate and $e_t$ is the Model 1 residual at t. Model 2, i.e., Eq. 14 provides estimation of the unknown parameters. While not wishing to be bound by the theory, we believe that the constraint given by Eq. 10b is very critical to achieving stable unbiased and accurate future predictions of BGC.

Applying this to the exemplary FBPC system in FIG. 1, $y_t$ is provided in Eq. 14 and which theoretically should equal the set point (i.e., the desired BGC), Model 1 is provided in Eq. 8, and Model 2 is provided in Eq. 15.

In a further embodiment of the invention and as one of skill in the art would appreciate, BGC is affected by many different disturbances. The three most significant non-invasive disturbances fall into one of three categories: stress, consumed energy (i.e., meals), and activities. To adequately control BGC through the feedforward predictive control method, each of these disturbances must be taken into account. Announcements of each could be included in order to predict the impact of each as previously discussed. However, a benefit of the FBPC system and methods is that they overcome the difficulties previously encountered with the FFC system and methods which required modeling disturbances.

Method of Controlling Insulin

The process control of the invention can be employed in the monitoring and regulation of BGC for patients, particularly patients suffering from type 1 diabetes mellitus. The process control scheme of the invention can be applied to an insulin delivery system as shown in FIGS. 2A and 2B, which comprise a computing device 8 comprising a processor 10, a machine readable non-transitory media 12 which stores the FBPC control 14 of the invention, and a monitoring system 2.

Preferably, the method employs a monitoring system 2, which monitors the various inputs (disturbances). For example, the monitoring system can provide information regarding the activity inputs ($X_A$ in FIGS. 3B and 3C), such as, skin temperature, near body temperature, and galvanic skin response. The monitoring system 2 can comprise one or more sensors capable of monitoring one of more of the inputs. In an aspect of the invention, the system can include a soft or virtual sensor monitoring, such as, heat flux. In an embodiment of the invention, the patient's basal and bolus are known from the insulin pump 2. For example, as bolus insulin can be administered by the insulin delivery system 4 and as the amount can be directed by the computing device 8, the amount of bolus insulin can be automatically logged. In a preferred embodiment, the methods are employed in an automatic insulin delivery system. An automatic insulin delivery system can be a system that monitors and instructs regarding insulin dosing, monitors and provides automatic insulin dosing, or an artificial pancreas.

Figure 2A:
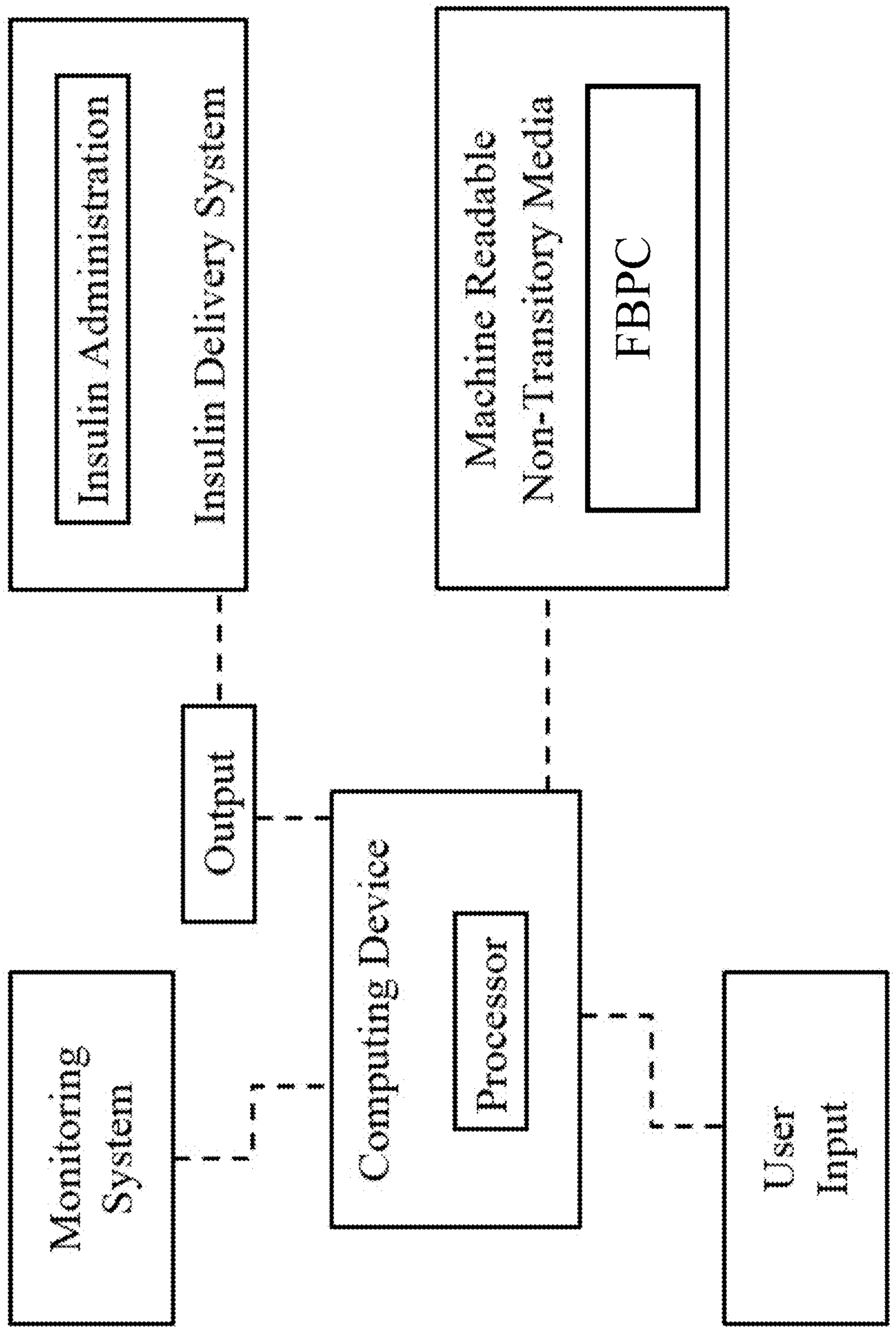
FIG. 2A shows a diagram of a system or method for controlling BGC according to the invention.
Figure 2B:
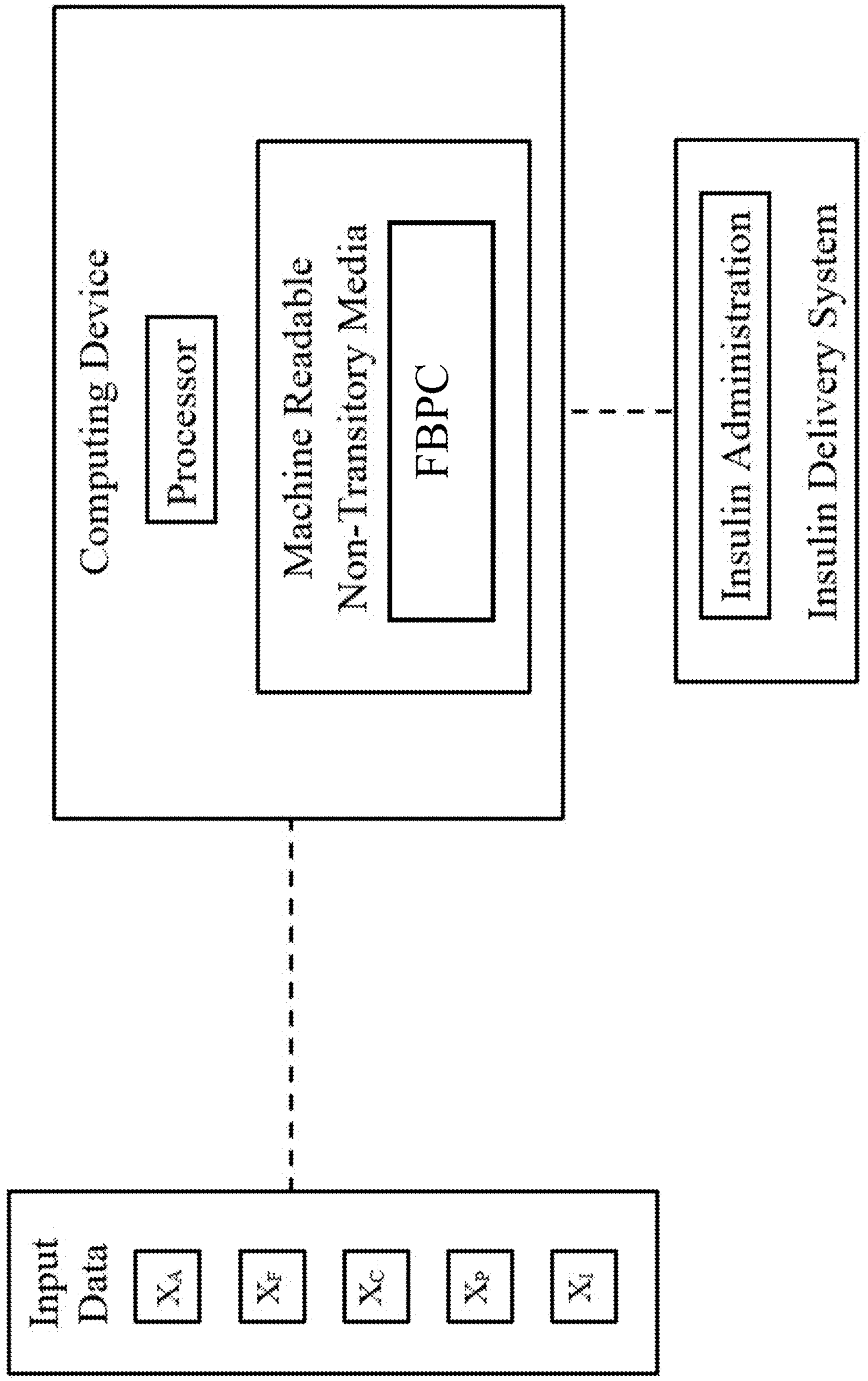
FIG. 2B shows a diagram of a system or method for controlling BGC according to the invention.

As shown in FIGS. 2A and 2B, both the user input 16 and monitoring system 2 are in operable communication with a computing device 8 that contains a processor 10. The computing device 8 is also in operable communication with a machine readable non-transitory media 12. The machine readable non-transitory media 12 can store the FBPC control 14. The inputs 16, 2 are parametrized by the FBPC controller 14 to provide an output 6 that directs the insulin delivery system 4 to administer insulin. It is to be understood that wireless transceivers may be used to communicate information from sensors to the computing device 8. The sensors may be associated with wearable devices, mobile devices, or other computing devices.

FIGS. 2A and 2B show the computing device 8 is also in operable communication with an insulin delivery system 4. The insulin deliver system can comprise a wearable device, an artificial pancreas, or a combination thereof. The insulin delivery system 4 can comprise an apparatus suitable for administering insulin. Any suitable apparatus for administering insulin can be employed, including, but not limited to, an automatic insulin pump, a remotely controlled insulin pump, an IV, a catheter, or an artificial pancreas. Any suitable insulin pump capable of communication with the control system can be used. Preferably, the control method of the invention uses a remotely controlled insulin pump. Selection of an insulin pump can be based on preferences of the user for other features. The user inputs 16 and inputs provided by the monitoring system 2 are parametrized by the model 14 stored on the machine readable non-transitory media 12, which is in operable communication with the computing device 8. The FBPC control 14 provides an output to the computing device 8 which in turn provides an output 6 (as shown in FIG. 2A) to the insulin delivery system 4, which can direct the insulin delivery system 4 to adjust the insulin flow rate or quantity of insulin via the feedback predictive control scheme. In some embodiments of the invention, the output 6 can be provided in any communicable form and recorded, printed, displayed, etc. such that there is a record of the output 6. In an embodiment of the invention where the basal and bolus insulin are automatically monitored the output 6 can be relayed back into the machine readable non-transitory media 12.

Embodiments of the invention can reduce the variance in blood glucose concentration of a patient by the use of a more accurate future feedback error by predicting BGC more accurately due to a much short prediction horizon leading to better adjustments of insulin flow rate due under feedback predictive control. In embodiments of the invention, when compared with existing methods of controlling blood glucose concentration, the reduction in variance can be greater than 50%, preferably greater than 60%, more preferably greater than 70%, or most preferably greater than 80%.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Utilizing a continuous stirred tank reactor (CSTR) as a process model, the methods of the present invention were tested to verify Equations 1-15 and the FBPC algorithm exemplified in the block diagram of FIG. 1A. The FBPC algorithm was tested against an algorithm employing a model predictive control system as shown in FIG. 1B.

A multiple-input, single-output Wiener model as shown in FIG. 3A was used in modeling the CSTR process. Each input, $X_i$, has its own linear dynamic block, $G_i$, and each dynamic block has an intermediate, unobservable output $V_i$, which represents the independent dynamic response of the corresponding input. The intermediate outputs are passed through a nonlinear static gain block, $f(V)$, to produce the final measured output, y.

Each dynamic block is a linear ordinary differential equation. In this Example, the manipulated variable, M, has first-order-plus-dead-time (FOPDT) dynamics shown in Eq. (16)

$$\tau_1 \frac{dv_1(t)}{dt} + v_1(t) = x_1(t - \theta_1) \tag{16}$$

where subscript '1' denotes the manipulated variable, $\tau_1$ is the time constant, and $\theta_1$ is the dead time. Using a backward difference approximation, an approximate discrete-time form of Eq. (16) is given in Eq. (17)

$$v_{1,t} = \delta_{1,1} v_{i,t-\Delta t} + (1 - \delta_{1,1}) x_{1,t-k_1\Delta t} \tag{17}$$

For $k_1$ steps into the future, Eq. (17) becomes Eq. (18):

$$v_{1,t+k_1\Delta t} = \delta_{1,1} v_{1,t+(k_1-1)\Delta t} + (1 - \delta_{1,1}) x_{1,t} \tag{18}$$

where $$\delta_{1,1} = \frac{\tau_1}{\tau_1 + \Delta t} \tag{19}$$

The two other input variables, $T_{ci}$ and $C_{Ai}$, have second-order-plus-dead-time-plus-lead (SOPDTPL) form as shown in Eq. 20 below (which corresponds to Eq. 1 above):

$$\tau_i^2 \frac{d^2 v_i(t)}{dt^2} + 2\tau_i \zeta_i \frac{dv_i(t)}{dt} + v_i(t) = \tau_{ai} \frac{dx_i(t-\theta)}{dt} + x_i(t - \theta_i) \tag{20}$$

where I=2 represents $T_{ci}$, I=3 represents $C_{Ai}$, $\tau_i$ is the time constant, $\zeta_i$ is the damping coefficient, $\tau_{ai}$ is the lead parameter, and $\theta_i$ is the dead time. Using a backward difference approximation applied to a sampling interval of $\Delta t$, an approximate discrete-time form of Eq. (20) is shown in Eq. (21) (corresponding to Eq. 2 above)

$$v_{i,t} = \delta_{1,t} v_{i,t-\Delta t} + \delta_{2,i} v_{i,t-2\Delta t} + \omega_{1,i} x_{i,t-K_i\Delta t} + \omega_{2,i} x_{i,t-(k_i+1)\Delta t} \tag{21}$$

where $\omega_{2,i}=1-\delta_{1,i}-\delta_{2,i}-\omega_{1,i}$ to satisfy the unity gain constraint with $$\delta_{1,i} = \frac{2\tau_i^2 + 2\tau_i \zeta_i \Delta t}{\tau_i^2 + 2\tau_i \zeta_i \Delta t + \Delta t^2} \tag{22}$$

$$\delta_{2,i} = \frac{-\tau_i^2}{\tau_i^2 + 2\tau_i \zeta_i \Delta t + \Delta t^2} \tag{23}$$

$$\omega_{1,i} = \frac{(\tau_{ai} + \Delta t)\Delta t}{\tau_i^2 + 2\tau_i \zeta_i \Delta t + \Delta t^2} \tag{24}$$

Equations 22-24 correspond to Equations 3-5 above. After obtaining $v_{i,t}$ for each input I, the modeled output value is determined by substituting these results into $f(V)$.

$$\eta_t = f(V) = a_0 + a_1 v_{1,t} + \ldots + a_p v_{p,t} + b_1 v_{1,t}^2 + \ldots + b_p v_{p,t}^2 + c_{1,2} v_{1,t} v_{2,t} + \ldots + c_{p-1,p} v_{p-1,t} v_{p,t} \tag{25}$$

Modification of Eq. (25) for predicting $k_1$ time steps into the future with p=3 gives $$\eta_{t+k_1\Delta t} = a_0 + a_1 v_{1,t+k_1\Delta t} + \ldots + a_3 v_{3,t+k_1\Delta t} + b_1 v_{1,t+k_1\Delta t}^2 + \ldots + b_3 v_{3,t+k_1\Delta t}^2 + c_{1,2} v_{1,t+k_1\Delta t} v_{2t+k_1\Delta t} + \ldots + c_{2,3} v_{2,t+k_1\Delta t} v_{3,t+k_1\Delta t} \tag{26}$$

where $a_i$, $b_i$, and $c_{i,j}$, denote the linear, quadratic and interaction parameters for I=1, 2, 3 and j=2 and 3, and $$v_{2,t+k_1\Delta t} = \delta_{1,2} v_{2,t+(k_1-1)\Delta t} + \delta_{2,2} v_{2,t+(k_1-2)\Delta t} + \omega_{1,2} x_{2,t+(k_1-k_2)\Delta t} + \omega_{2,2} x_{2,t+(k_1-k_2-1)\Delta t} \tag{27}$$

$$v_{3,t+k_1\Delta t} = \delta_{1,3} v_{3,t+(k_1-1)\Delta t} + \delta_{2,3} v_{3,t+(k_1-2)\Delta t} + \omega_{1,3} x_{3,t+(k_1-k_3)\Delta t} + \omega_{2,3} x_{3,t+(k_1-k_3-1)\Delta t} \tag{28}$$

In this Example, all measured inputs are assumed to be known over the prediction horizon.

To model unmeasured disturbances and bias, a noise model structure was applied to Eq. (25) as follows:

$$y_t = \eta_t + N_t, \tag{26}$$

where $$N_t = \frac{\theta_q(B)}{\phi_p(B)} a_t = \tag{27}$$

$$\frac{1 - \theta_1 B - \theta_2 B^2 - \ldots - \theta_q B^q}{1 - \phi_1 B - \phi_2 B^2 - \ldots - \phi_p B^p} a_t = \frac{a_t}{\Phi(B)} = \frac{a_t}{\left[1 - \varphi_1 B - \varphi_2 B^2 - \ldots\right]} \ \forall\, t$$

$$a_t \overset{indep}{\sim} N(0, \sigma^2) \tag{28}$$

and $y_t$ is the measured tank temperature, $T_m$, at t and $B^\gamma x_t = x_{t-\gamma\Delta t}$.

Then $$y_t\left[1 - \varphi_1 B - \varphi_2 B^2 - \ldots\ \right] = \eta_t\left[1 - \varphi_1 B - \varphi_2 B^2 - \ldots\ \right] + a_t \tag{29}$$

$$\Rightarrow y_t = \eta_t + \varphi_1(y_{t\Delta t} - \eta_{t\Delta t}) + \varphi_2(y_{t2\Delta t} - \eta_{t2\Delta t}) + \ldots + a_t \tag{30}$$

Modification of Eq. (30) for predicting $k_1$ time steps into the future gives $$\hat{y}_{t+k_1\Delta t} = \hat{\eta}_{t+k_1\Delta t} + \hat{\varphi}_1(y_t - \hat{\eta}_t) + \hat{\varphi}_2(y_{t-\Delta t} - \hat{\eta}_{t-\Delta t}) + \tag{31}$$

$$= \hat{\eta}_{t+k_1\Delta t} + \hat{\varphi}_1 e_t + \hat{\varphi}_2 e_{t-\Delta t} +$$

where "^" is used for estimate. $\hat{\eta}_{t+k_1\Delta t}$ is called Model 1 and $\hat{y}_{t+k_1\Delta t}$ is called Model 2. In this Example, since the input values, as well as the current and past values of the controlled variable, are known, Eq. 31 has all the necessary information to predict the value of the controlled variable at $t+k_1\Delta t$ (i.e., $t+\theta_1$) time in the future.

The block diagrams of the two virtual sensor predictive control algorithms are shown in FIGS. 1 & 2. A description of the transfer functions in the blocks is given in Table 1.

TABLE 1

| Transfer Function | Description |
|---|---|
| $G_c$ | Controller |
| $G_v$ | Valve |
| $G_p$ | Process |
| $G_{Li}$ | Load i |
| $G_m$ | Transmitter for the controlled variable |
| $K_m$ | Transmitter gain for the controlled variable |

For each of the systems, a change in the manipulated variable at t affects the controlled variable $k_1\Delta t$ time into the future. As shown in FIG. 1, for FBPC the controller is a common PID controller, and thus can have a three-dimensional tuning space. The FBE requires the predicted value of the controlled variable $k_1\Delta t$ time into the future, the time when current change in the manipulated variable affects the output. In contrast to FBPC, MPC has one tuning parameter, J, representing the number of time steps beyond $t+k_1\Delta t$ when the multiple-input model of the controlled variable (i.e., $\hat{y}_{t+(k_1+J)\Delta t}$) equals the set point for the next change. Thus, MPC requires prediction farther into the future than FBPC, and hence, its FBE, will likely be less accurate. Also, as shown in FIG. 2, the MPC control law uses the inverse of a one-input controlled variable model ($\hat{G}_{VP}$), to determine the next control move. Hence, it is critical that this model has an accurate causative relationship, which can be difficult to achieve in practice.

Figure 4:
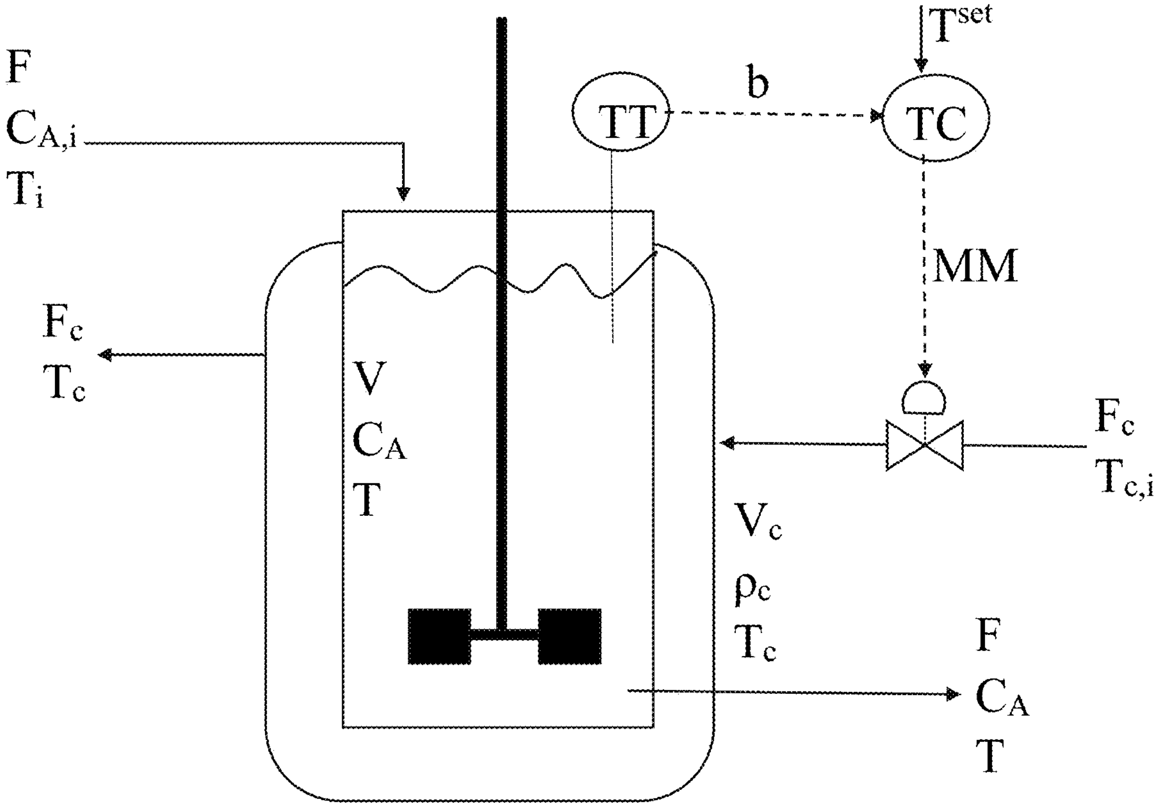
FIG. 4 shows the model CSTR used in Example 1.

The CSTR process used in this Example is illustrated in FIG. 4 and described by Eqs. 32-36. The definitions and values of the variables are outlined in Table 2.

$$\frac{dC_A}{dt} = \frac{F}{V}(C_{Ai} - C_A) - kC_A^2 \tag{32}$$

$$\frac{dT_T}{dt} = \frac{F}{V}(T_T - T_T) - \frac{\Delta H_R}{\rho C_p} kC_A^2 - \frac{UA}{\rho V C_p}(T_T - T_C) \tag{33}$$

$$\frac{dT_C}{dt} = \frac{UA}{V_C \rho_C C_{pC}}(T_T - T_C) - \frac{F}{V_C}(T_C - T_{Ci}) \tag{34}$$

$$k = k_0 \exp\left(\frac{-E}{R(T_T + 273.16)}\right) \tag{35}$$

$$F_C = F_{Cmax} \times \alpha^{(-M)} \tag{36}$$

TABLE 2

| Variable | Definition | SS value (units) |
|---|---|---|
| A | Heat transfer area | 5.40 ($m^2$) |
| $\alpha$ | Control valve rangeability parameter | 50 (none) |
| $C_A$ | Concentration of species A in reactor | 1.0302 (kgmol/$m^3$) |
| $C_{Ai}$ | Concentration of species A in inlet stream | 2.88 (kgmol/$m^3$) |
| $c_p$ | Heat capacity of feed and product streams | $1.815 \times 10^5$ (J/kgmol-° C.) |
| $c_{pc}$ | Heat capacity of coolant | 4184 (J/kg-° C.) |
| $\Delta H_R$ | Heat of reaction | $-9.86 \times 10^7$ (J/kgmol) |
| E | Activation energy | $1.182 \times 10^7$ (J/kgmol) |
| F | Feed flow rate | 0.45 ($m^3$/s) |
| $F_C$ | Coolant flow rate | 0.44 ($m^3$/s) |
| $F_{Cmax}$ | Maximum flow rate of coolant through control valve | 1.2 ($m^3$/s) |
| K | Reaction rate constant | 0.09 ($m^3$/s-kgmol) |
| $k_o$ | Arrhenius frequency parameter | 0.0744 ($m^3$/s-kgmol) |
| M | Input signal to the valve subject to $0 \le M \le 1$ | 0.26 (none) |
| R | Gas law constant | 8314.39 (J/kgmol-K) |
| $\rho$ | Density of reactor contents | 19.2 (kgmol/$m^3$) |
| $\rho_c$ | Density of coolant | 1000 (kg/$m^3$) |
| $T_c$ | Coolant temperature in the jacket | 50.48 (° C.) |
| $T_{Ci}$ | Coolant inlet temperature | 27 (° C.) |
| T | Reactor temperature | 88 (° C.) |
| $T_m$ | Measured reactor temperature | 88 (° C.) |
| U | Overall heat transfer coefficient | $2.13 \times 10^5$ (J/s-$m^2$-° C.) |
| $V_C$ | Cooling jacket volume | 1.82 ($m^3$) |
| V | CSTR volume | 7.08 ($m^3$) |

In this Example, three input variables are used in the model. They are: 1) the input signal to the valve, M; 2) the temperature of the entering coolant, $T_{ci}$; and 3) the concentration of component A in the inlet stream, $C_{Ai}$. There is one unmeasured disturbance, the feed flow rate, F. There is one output for this Example, the measured tank temperature, $T_m$. The CSTR is altered to include dead time, $\theta_i$, in $T_{ci}$, $C_{Ai}$, and the input signal to valve, M, specified as $\theta_i = k_i\Delta t$, where $k_i$ is a positive integer, I=1, 2, or 3, for M, $T_{ci}$, and $C_{Ai}$, respectively. The dead time for M is the largest.

Figure 5:
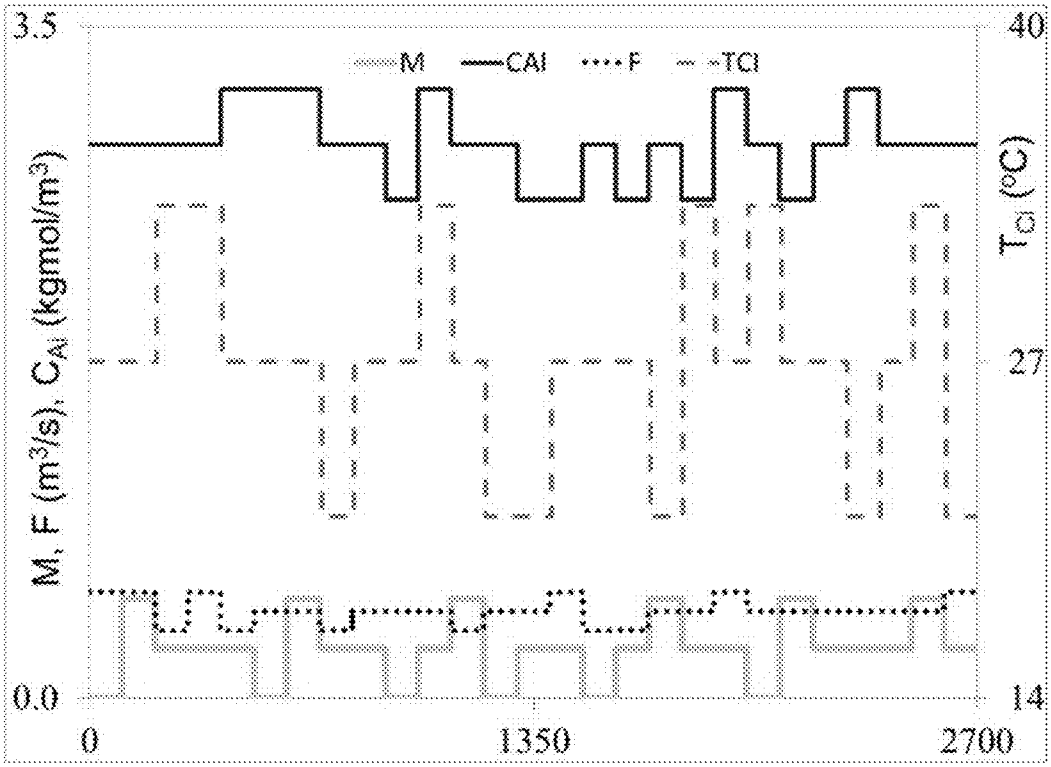
FIG. 5 shows the training input sequences for M, $T_{ci}$ and $C_{Ai}$ from Example 1.

The training input sequences for M, $T_{ci}$ and $C_{Ai}$ are shown in FIG. 5. The fits for this training data are shown in FIGS.

Figure 6:
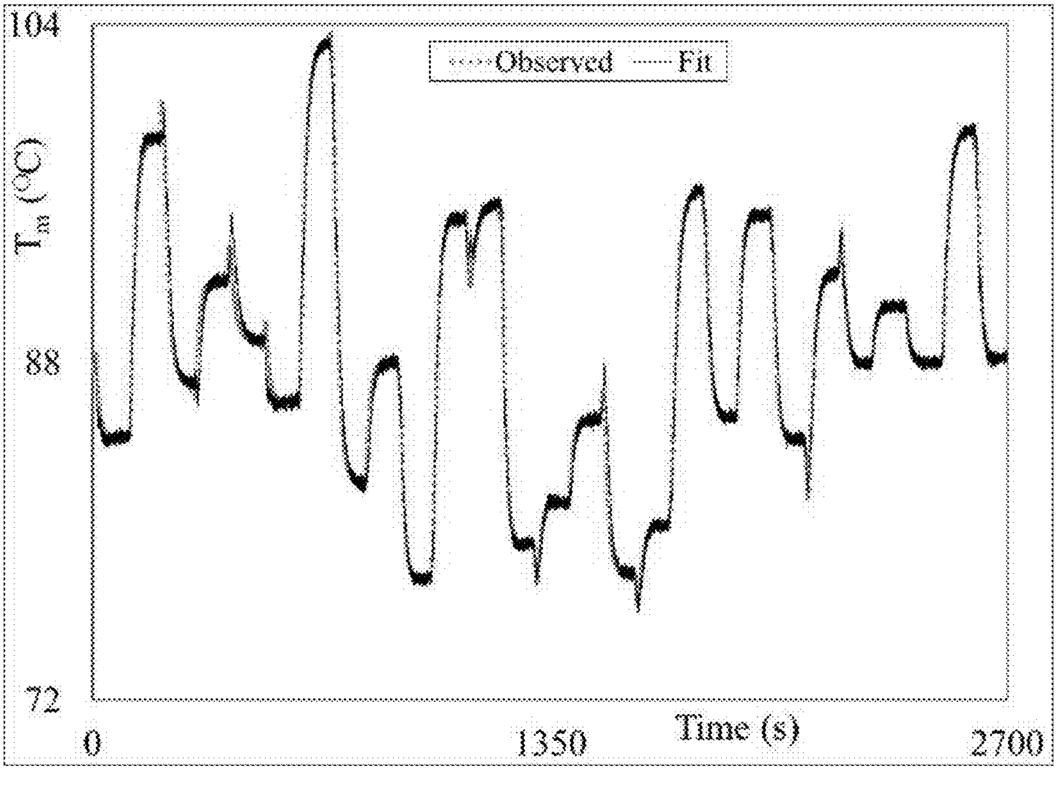
FIG. 6 shows the fit for the training data with Model 2 as given by Eq. 27.
Figure 7:
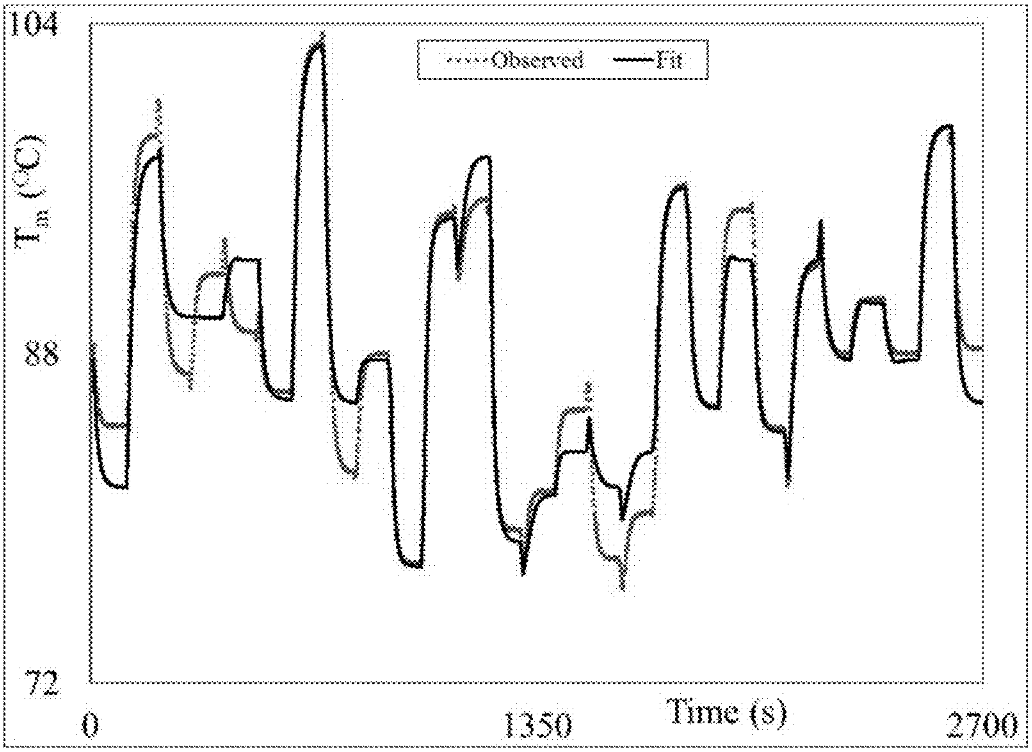
FIG. 7 shows the fit for the training data with Model 1, the input-only model.

6 and 7. FIG. 6 shows the excellent fit of Model 2, the model that fits the inputs and the serial correlation structure of the noise, the unmeasured disturbances, and the model bias, as given by Eq. (27). This is the model used in the control algorithms. The fit shown in FIG. 7 is a fit of the input-only Model 1. Thus, it does not fit the unmeasured disturbance, and as a result, this fit is very poor, given the large changes in the feed rate, F.

Figure 8A:
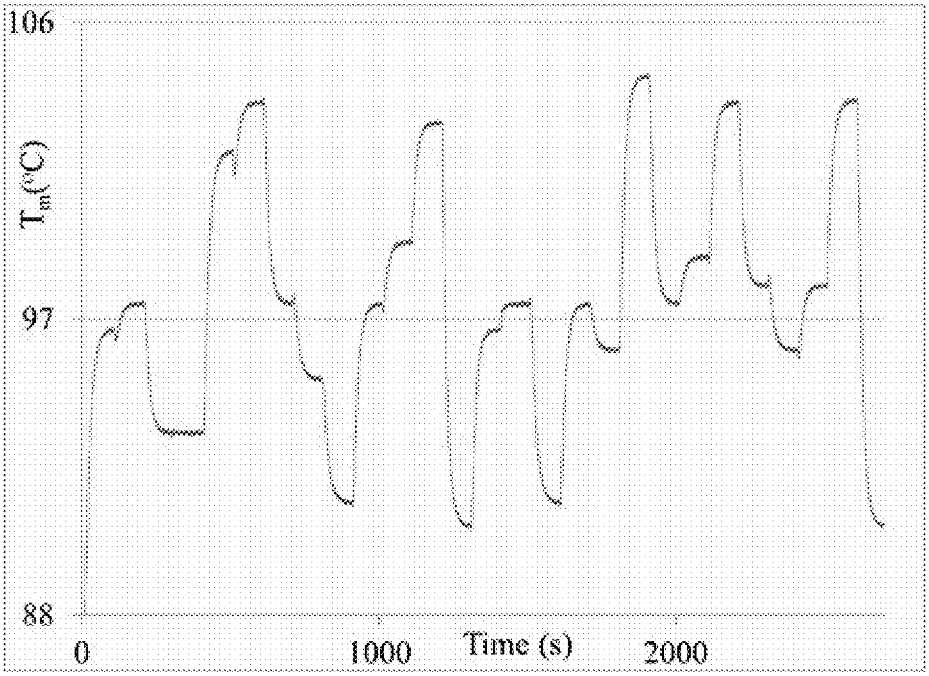
FIG. 8A shows the response of the measured reactor temp, $T_m$, the variable to be controlled, when the input signal to the valve, M, is fixed at its initial value.
Figure 8B:
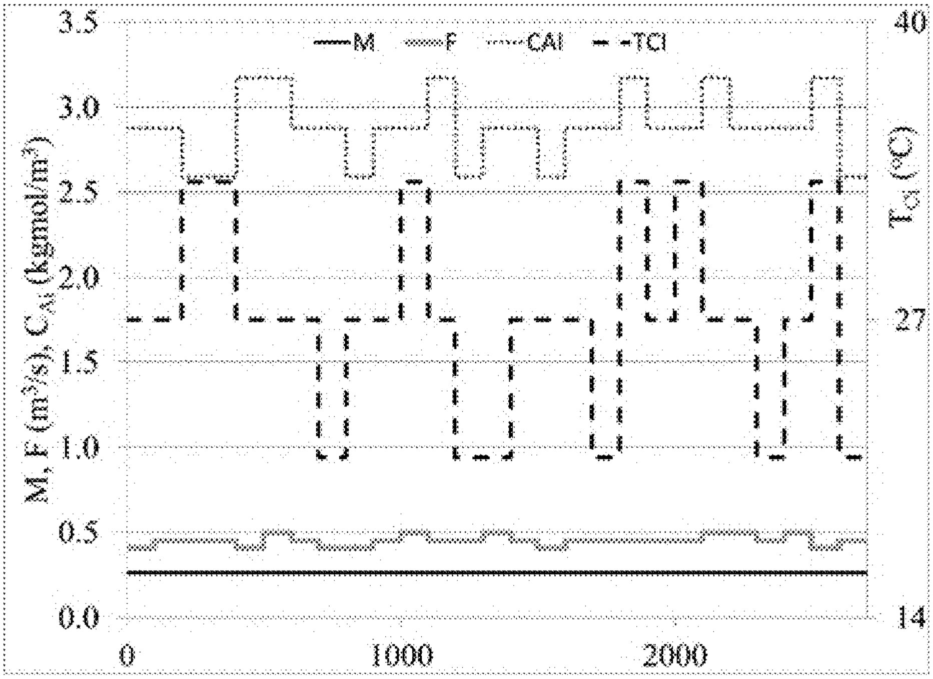
FIG. 8B shows the input signal to the valve, M, fixed at its initial value and with changed input variables as if for a control run.

In this Example, $k_1\Delta t$, $k_2\Delta t$ and $k_3\Delta t$ are 10 seconds, 5 seconds, and 0 seconds with $\Delta t=0.1$ seconds, thus the predictions for each control method are at least 100 time steps into the future. FIG. 8A shows the response of the measured reactor temp, $T_m$, the variable to be controlled, when the input signal to the valve, M, is fixed at its initial value (as shown in FIG. 8B). The other input variables are changed as shown in FIG. 8B as if for the control run.

The objective is to minimize the variation of $T_m$ around the set point by manipulating the input signal to the valve, M, subject to $0 \le M \le 1$. To correct for bias, the common practice for MPC applications is to use a bias correction that is the latest measurement of $T_m$ minus its corresponding predicted value. When the MPC estimator was used in the bias correction, the results were poor. This is shown as "MPC-BC" in Table 3. In addition, when these differences as the residuals were used for Model 2 in the MPC algorithm, control was also poorer than FBPC. The best results for MPC were obtained using Model 2 to correct for bias. These control results along with the ones for FBPC are given in Table 3.

TABLE 3

| Control Method | J | Stdev (° C.) | % Increase from FBPC |
|---|---|---|---|
| FBPC | NA | 0.41 | 0 |
| MPC | 10 | 0.49 | 18 |
| | 15 | 0.49 | 18 |
| | 20 | 0.49 | 18 |
| | 30 | 0.48 | 17 |
| MPC--BC | 30 | 0.96 | 132 |

Figure 9A:
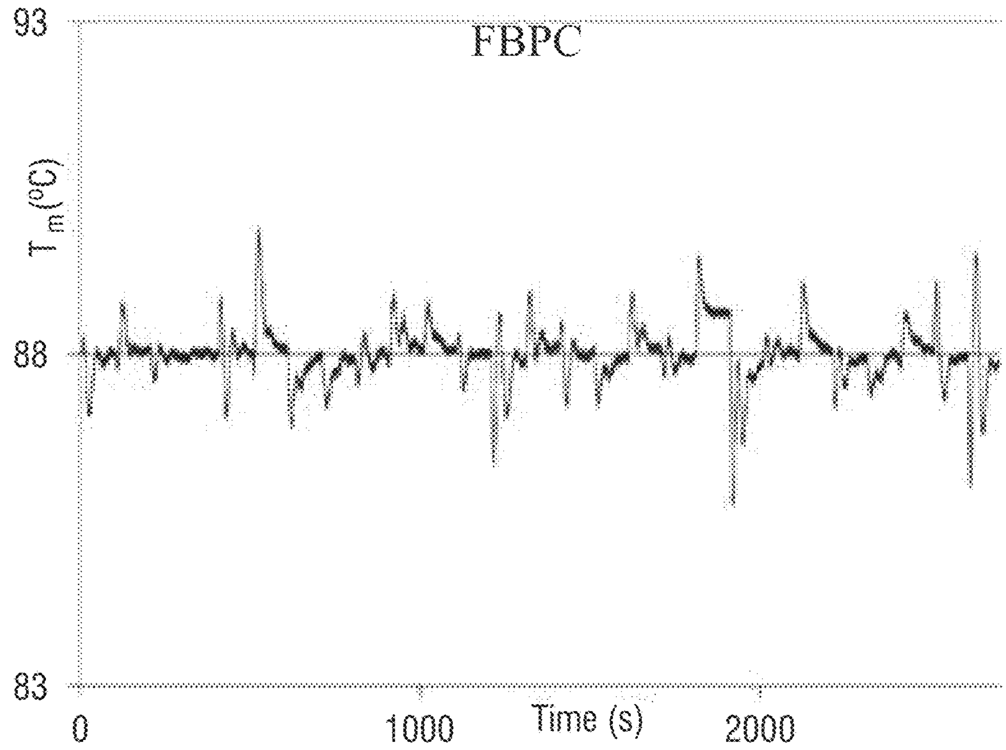
FIGS. 9A and 9B show the $T_m$ and M results, respectively, for the FBPC in Example 1.
Figure 9B:
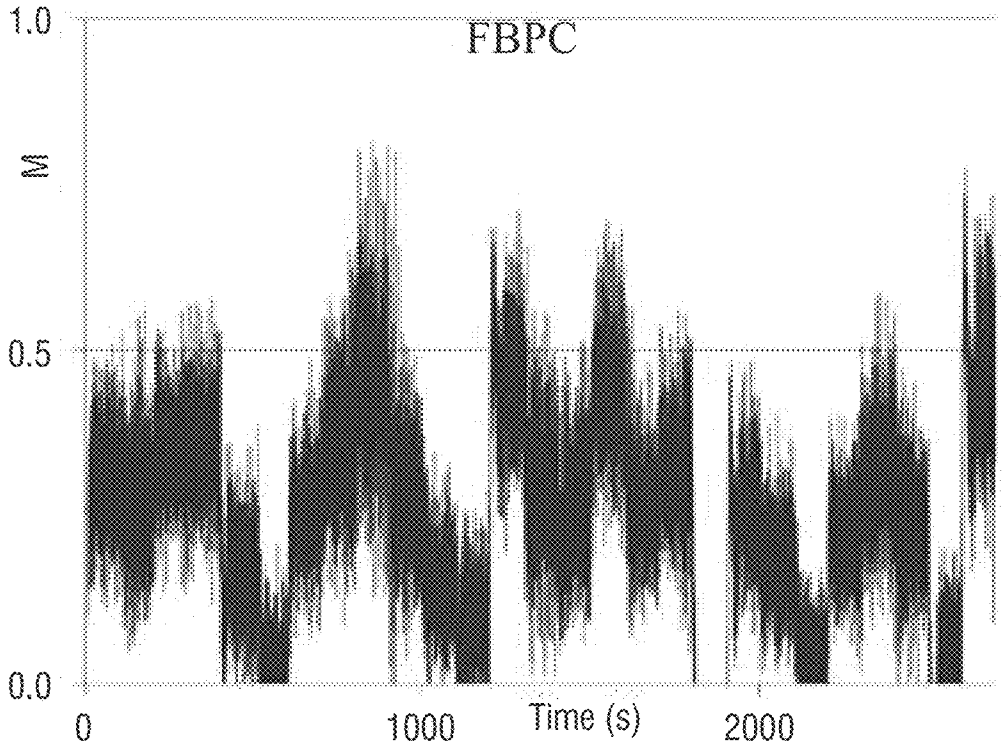
Figure 9C:
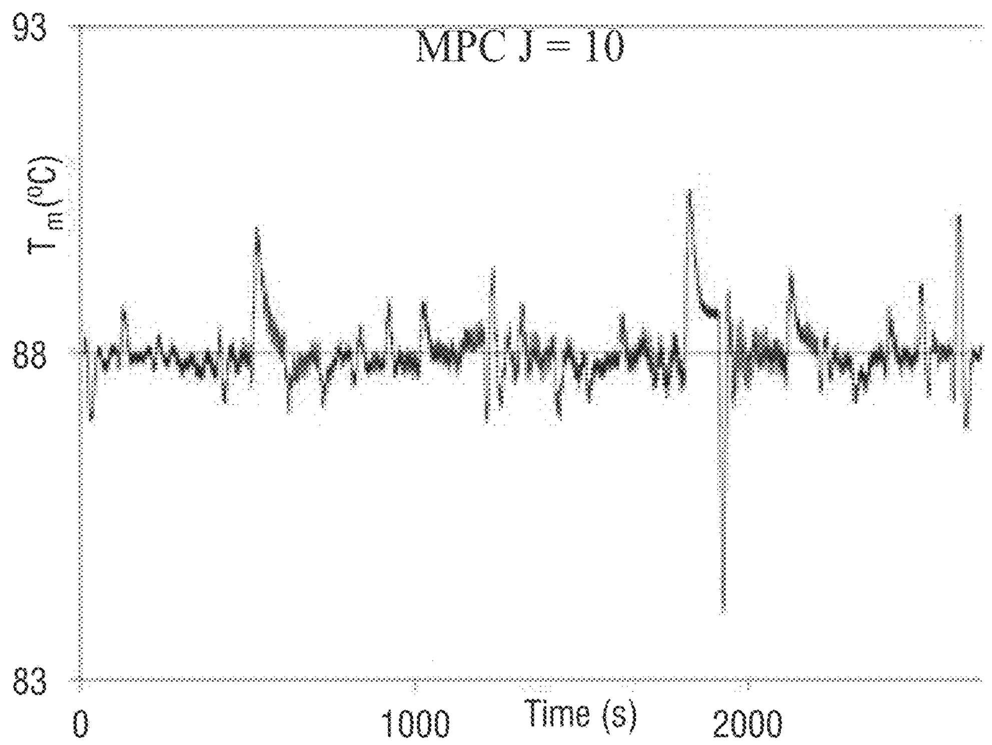
FIGS. 9C and 9D show the $T_m$ and M results, respectively, for the MPC where J=10 in Example 1.
Figure 9D:
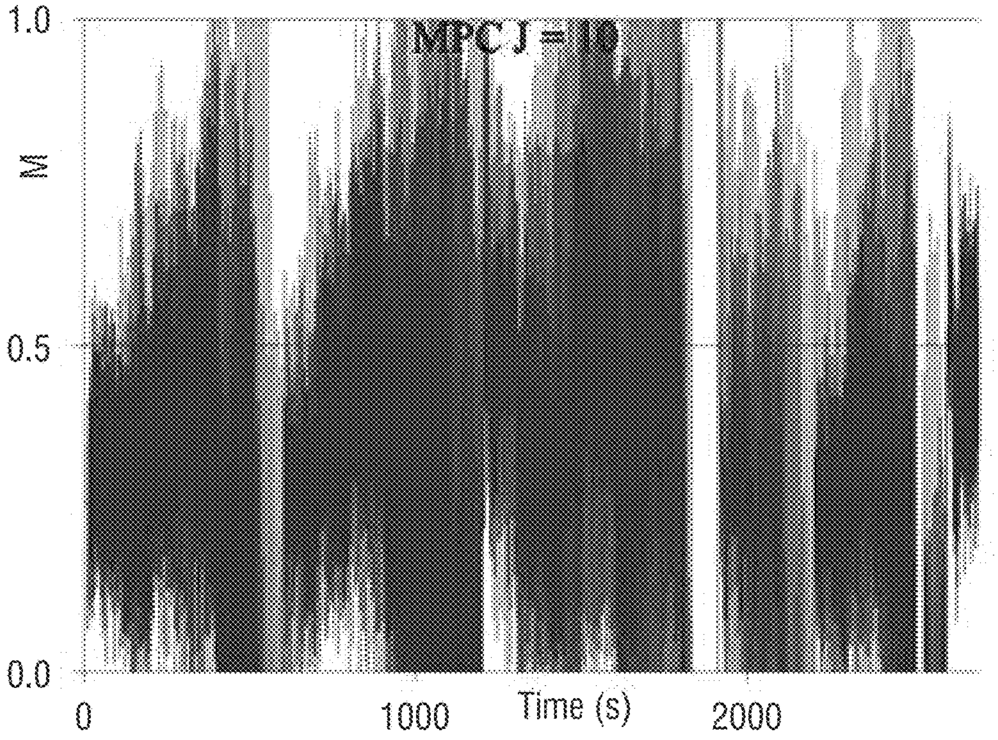
Figure 9E:
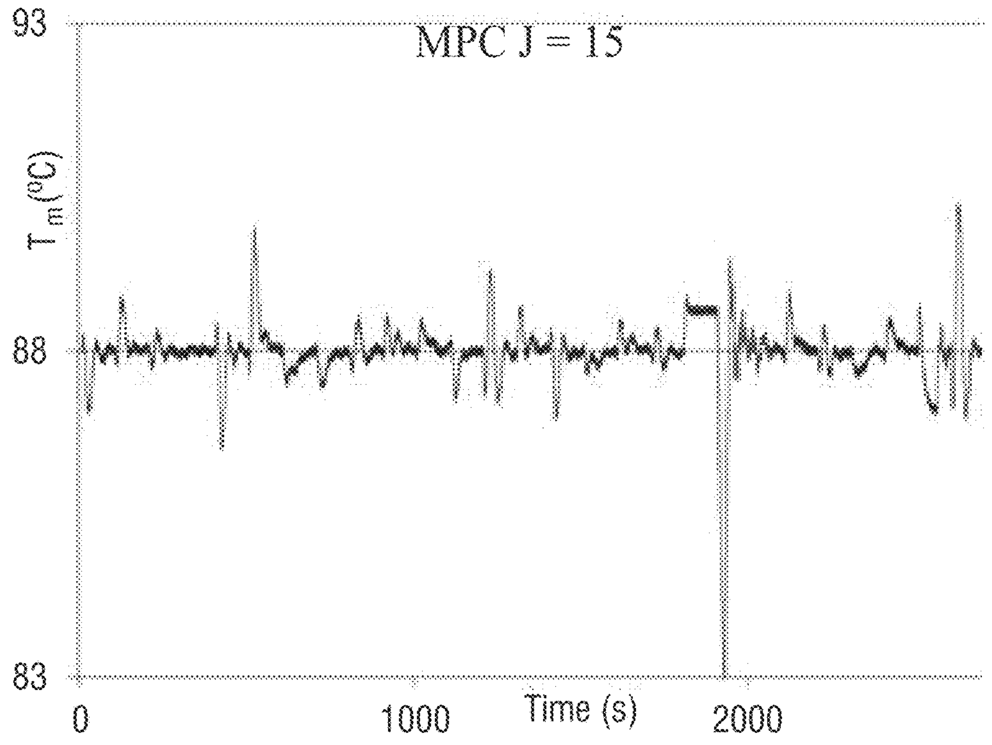
FIGS. 9E and 9F show the $T_m$ and M results, respectively, for the MPC where J=15 in Example 1.
Figure 9F:
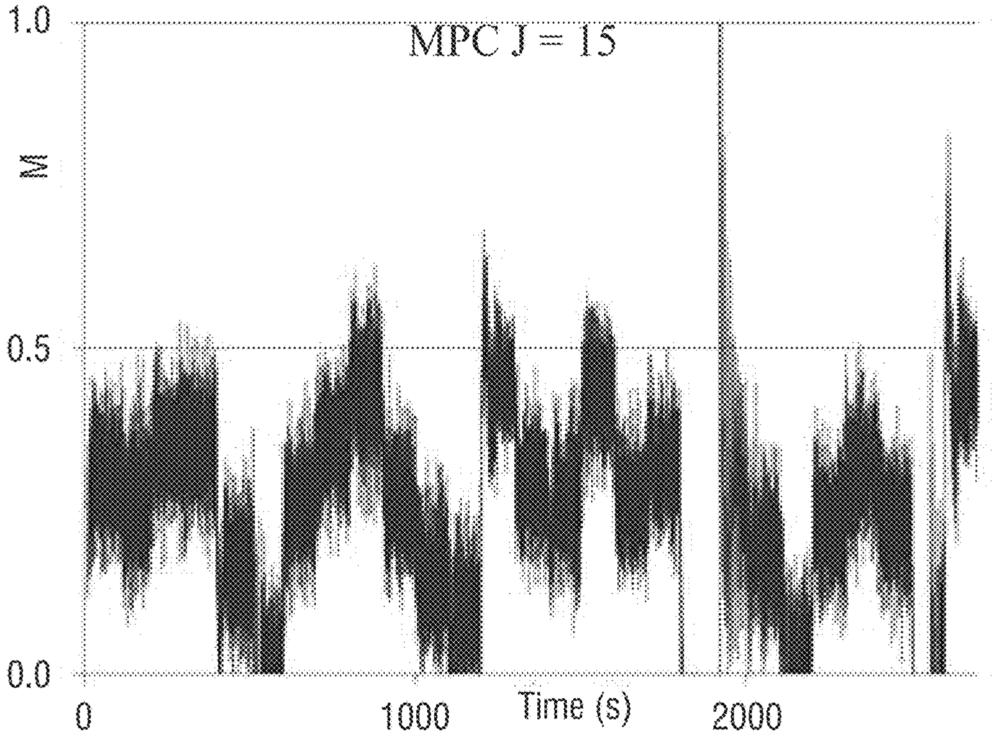

As shown in Table 3, FBPC has the smallest Stdev. MPC for J=10, 15, 20, and 30 are all similar and about 20% worse than FBPC. Note that for these values of J, MPC is only predicting 1 to 3 seconds farther into the future. Thus, for such a short distance into the future and the high accuracy of the fitted model, the improvement in FBPC is not expected to be too much greater than MPC, as the results indicate. $T_m$ and M results for FBPC are shown in FIGS. 9A and 9B, respectively. The $T_m$ and M results for MPC where J=10 and 15, are shown in FIGS. 9C-9F. In going from J=10 to 15, M for MPC is more aggressive than FBPC. Thus, even with more aggressiveness in the manipulated variable, MPC control performance is worse than FBPC. The MPC case with bias correction, representing the current practice, denoted by 'MPC-BC' in Table 3, is 132% worse than FBPC. Thus, Model 2 helped the control of MPC substantially over the bias correction method but MPC results are still worse than FBPC.

Example 2

In this Example, the present invention's modeling approach is shown to accurately predict BGC 30 and 60 minutes into the future for Type 1 diabetes subjects, which is necessary to obtain an accurate prediction of FBE to effectively manipulate insulin flow rate at the present time for optimal control of BGC. This Example is an open-loop modeling study, and not a closed-loop control study.

For this Example, the process model utilizes a Wiener model with a semi-coupled network for BIC and BGC as illustrated in FIG. 3B. The semi-coupled network allows modeling of blood insulin infusion rate and glucose interaction. BIC is not measured, and therefore the approach uses a "pseudo" BIC variable that allows the use of a modeling structure that is hypothesized to provide characteristics for BGC that are more physiologically correct than a Wiener-only modeling technique.

This Example employs the two-step modeling approach outlined in Example 1: applying a noise model structure (Model 2) to model unmeasured disturbances and bias in the predictive model (Model 1). Model 1 uses the network illustrated in FIG. 3B. As shown all inputs, $X_i$, pass through a linear dynamic block to produce the unobservable dynamic output variables, $V_i$. Note that $I=A_i \ldots A_p$ for p activity inputs, C for carbohydrates, F for fats, P for proteins, and I for insulin. The dynamic blocks for the inputs have SOPDTPL for as shown in Example 1 Eqs. (20)-(24). A dynamic mass balance on the $G_{FI}$ block in FIG. 3B, which represents the BGC due to food and insulin only, is shown in Eq. (37)

$$\frac{dV_{FI}(t)}{dt} = a_C v_C(t) + a_F v_F(t) + a_P v_P(t) - a_{FI} I(t) V_{FI}(t) \tag{37}$$

where $a_C$, $a_F$, and $a_{FI}$, are estimated model parameters, I(t) is the unmeasured BIC at time t, and $V_{FI}(t)$ is the BGC due to food and insulin changes only. Similarly, a dynamic mass balance on the $G_{BI}$ block, which represents BIC is shown in Eq. (38)

$$\frac{dI(t)}{dt} = a_I v_I(t) - a_{BI} I(t) \tag{38}$$

where $a_I$ and a $B_{BI}$ are estimated model parameters. The function $f(V)$ is a first-order linear regression structure given in discrete form in Eq. (39)

$$f(V) = \eta_i + \varepsilon_t = a_0 + V_{FI,t} + a_{A1} v_{A_1,t} + \ldots + a_{Ap} v_{A_p,t} \tag{39}$$

where $a_0$ and $a_{Ai}$'s are static estimated parameters.

Unmeasured disturbances and bias, Model 2, is as described mathematically in Example 1, Eqs. (26)-(31), subject to one constraint as described in Eqs. (40) and (41) (corresponding to equations 10a and 10b above), which is critical to achieving stable unbiased and accurate future prediction of BGC.

$$N_t = \frac{\theta_q(B)}{\phi_p(B)} a_t = \tag{40}$$

$$\frac{1 - \theta_1 B - \theta_2 B^2 - \ldots - \theta_q B^q}{1 - \phi_1 B - \phi_2 B^2 - \ldots - \phi_p B^v} a_t = \frac{a_t}{\Phi(B)} = \frac{a_t}{[1 - \varphi_1 B - \varphi_2 B^2 - \ldots]} \forall t$$

subject to $$\sum \varphi_i = 1 \tag{41}$$

In this Example, the model was fit to eleven cases of BGC subject data split into sets of training, validation, and testing. The model parameters are estimated using the training data, and the validation set is used to guard against over-fitting, as the final set of parameters must maximize the fit in this set. Since these two sets influence the parameter estimation process, the testing set is used as a final check on model fit, as the data in this set has no influence on the values of the estimated parameters. This Example applies Model 2 under the following conditions for the training data sets:

$$\min_{\hat{\phi}_i} SSE = \sum_{over\ training\ time} e_t^2 \tag{42}$$

subject to $$\sum_{i=1}^{4} \hat{\varphi}_i = 1 \tag{43}$$

Thus, four $\hat{\varphi}$ were used in each case and convergence criterion is given in Eq. (42) and subject to Eq. (43). In this Example using Model 2, all the data not used to determine the $\hat{\varphi}_i$'s is testing data.

The results for this Example are reported using three metrics. The first is the correlation coefficient between the fitted and measured BGC, $r_{fit}$, and is given by Eq. (44):

$$r_{fit} = \frac{\sum_{i=1}^{n_t} y_i \hat{y}_i - \frac{\left(\sum_{i=1}^{n_t} y_i\right)\left(\sum_{i=1}^{n_t} \hat{y}_i\right)}{n_t}}{\sqrt{\sum_{i=1}^{n_t} y_i^2 - \frac{\left(\sum_{i=1}^{n_t} y_i\right)^2}{n_t}} \sqrt{\sum_{i=1}^{n_t} \hat{y}_i^2 - \frac{\left(\sum_{i=1}^{n_t} \hat{y}_i\right)^2}{n_t}}} \tag{44}$$

where $n_t$ is the number of pairs of values in the set, and $y_i$ and $\hat{y}_i$ are the $i^{th}$ measured and fitted values in the set, respectively. The closer this statistic is to 1.0, the better the model fits the measured response data without consideration of model bias.

The second statistic is the averaged difference, AD, which gives a measure of model bias. As shown in Eq. (45), it is the average of deviation for the differences of $y_i$ and $\hat{y}_i$.

$$AD = \frac{1}{n_t} \sum_{i=1}^{n_t} (y_i - \hat{y}_i) \tag{45}$$

The final statistic is the averaged absolute error, AAD, and is a measure of the average closeness of $y_i$ and $\hat{y}_i$, as shown in Eq. (46).

$$AAD = \frac{1}{n_t} \sum_{i=1}^{n_t} (y_i - \hat{y}_i) \tag{46}$$

The 13 variable input set is given in Table 4 and consists of three food nutrients, seven activity variables and two for insulin infusion. The activity variables were collected using the SenseWear® Pro3 Body Monitoring System shown in FIG. 14, which is worn on the triceps of the subject's arm. The SenseWear® armband utilizes pattern detection algorithms that employ physiologic signals from a unique combination of sensors to generate values for 20 activity variables. The armband collects data using a two-axis accelerometer and four sensors that are used to determine heat flux, skin temperature, near body temperature, and galvanic skin response. The two-axis accelerometer provides information about body position and tracks upper arm movement. The heat flux sensor calculates the amount of heat being dissipated from the body by measuring the amount of heat lost along a thermally-conductive path between the skin and a vent on the side of the armband. Skin temperature and near-body temperature are measured by sensitive thermistors, and galvanic skin response is measured via the conductivity of the subject's skin as it varies due to physical and emotional stimuli. Measurements were taken at five-minute intervals. The data collection was conducted over the course of a year by an experienced graduate student.

TABLE 4

| Food Inputs | Activity Inputs | Circadian Rhythm | Insulin Inputs |
|---|---|---|---|
| 1 = Carbohydrates | 4 = Transverse acceleration (peaks) | 11 = Time of Day (TOD) | 12 = Bolus |
| 2 = Fats | 5 = Heat Flux (avg) | | 13 = Basal |
| 3 = Proteins | 6 = Longitudinal acceleration (avg) | | |
| | 7 = Near body temperature | | |
| | 8 = Transverse acceleration (MAD) | | |
| | 9 = GSR (avg) | | |
| | 10 = Energy expenditure | | |

The results of the predictive modeling approach 30 and 60 minutes into the future are outlined in Tables 5 and 6, respectively, with the data split into three sets comprising of one week of training, four days of validation, and three days of testing. Tables 7 and 8 show results for modeling 30 and 60 minutes into the future, respectively, with the data split into two sets: one week of training and one week of validation.

TABLE 5

| | 7 Day Training | | | 4 Day Validation | | | 3 Day Test | | |
|---|---|---|---|---|---|---|---|---|---|
| Subject | AD | AAD | rfit | AD | AAD | rfit | AD | AAD | rfit |
| 1 | −0.4 | 16.2 | 0.95 | −0.3 | 19.5 | 0.93 | 0.7 | 15.8 | 0.96 |
| 2 | 0.3 | 20.6 | 0.96 | −1.6 | 22.0 | 0.94 | −0.5 | 26.7 | 0.94 |
| 3 | 0.8 | 24.0 | 0.92 | −0.6 | 25.4 | 0.89 | 0.5 | 22.6 | 0.90 |
| 4 | −0.1 | 17.4 | 0.87 | −0.3 | 23.4 | 0.90 | 0.1 | 18.0 | 0.89 |
| 5 | 0.1 | 26.2 | 0.92 | 1.2 | 29.6 | 0.94 | −2.2 | 26.4 | 0.92 |
| 6 | 0.0 | 17.2 | 0.95 | 0.6 | 14.9 | 0.97 | −0.1 | 14.8 | 0.93 |
| 7 | −0.1 | 21.3 | 0.93 | −0.9 | 19.6 | 0.87 | 0.9 | 19.6 | 0.95 |
| 8 | −0.1 | 15.3 | 0.90 | 0.1 | 22.7 | 0.83 | 1.8 | 18.3 | 0.90 |
| 9 | 0.4 | 18.7 | 0.95 | 0.2 | 23.5 | 0.91 | 0.0 | 18.1 | 0.96 |
| 10 | −0.3 | 18.4 | 0.95 | −0.6 | 17.0 | 0.95 | 0.6 | 25.5 | 0.92 |
| 11 | −0.3 | 17.9 | 0.93 | 1.4 | 20.3 | 0.93 | −0.7 | 19.4 | 0.95 |
| Average | 0.0 | 19.4 | 0.93 | −0.1 | 21.6 | 0.91 | 0.1 | 20.5 | 0.93 |

TABLE 6

| | 7 Day Training | | | 4 Day Validation | | | 3 Day Test | | |
|---|---|---|---|---|---|---|---|---|---|
| Subject | AD | AAD | rfit | AD | AAD | rfit | AD | AAD | rfit |
| 1 | −1.2 | 29.0 | 0.84 | −1.6 | 31.3 | 0.85 | 1.4 | 26.4 | 0.91 |
| 2 | 0.9 | 33.5 | 0.91 | −5.1 | 34.8 | 0.86 | −1.9 | 42.2 | 0.86 |
| 3 | 1.3 | 37.2 | 0.82 | −1.1 | 42.6 | 0.72 | 0.9 | 37.9 | 0.77 |
| 4 | −0.3 | 25.5 | 0.73 | −0.4 | 38.8 | 0.70 | −0.1 | 29.4 | 0.76 |
| 5 | 0.5 | 41.6 | 0.82 | 2.0 | 48.4 | 0.85 | −3.6 | 36.3 | 0.87 |
| 6 | 0.7 | 31.1 | 0.86 | 0.8 | 25.0 | 0.91 | −0.3 | 25.1 | 0.80 |
| 7 | −0.5 | 37.0 | 0.83 | −2.4 | 37.2 | 0.70 | 2.1 | 37.2 | 0.85 |
| 8 | −0.1 | 23.9 | 0.77 | 0.1 | 29.9 | 0.74 | 3.3 | 28.0 | 0.80 |
| 9 | 0.6 | 30.6 | 0.87 | 1.0 | 37.2 | 0.82 | 0.7 | 31.2 | 0.88 |
| 10 | −0.7 | 30.1 | 0.86 | −0.6 | 30.1 | 0.85 | 1.2 | 38.1 | 0.85 |
| 11 | −1.0 | 26.1 | 0.86 | 2.5 | 29.3 | 0.85 | 1.3 | 29.6 | 0.90 |
| Average | 0.0 | 31.4 | 0.83 | −0.4 | 35.0 | 0.80 | 0.2 | 32.9 | 0.84 |

TABLE 7

| | Training | | | Validation | | |
|---|---|---|---|---|---|---|
| Subject | AD | AAD | rfit | AD | AAD | rfit |
| 1 | −0.4 | 15.5 | 0.95 | 0.5 | 18.1 | 0.94 |
| 2 | 0.5 | 25.0 | 0.95 | 1.7 | 24.3 | 0.94 |
| 3 | 0.5 | 23.2 | 0.93 | 0.5 | 22.2 | 0.91 |
| 4 | 0.0 | 17.5 | 0.88 | −0.3 | 20.4 | 0.90 |
| 5 | −0.3 | 25.3 | 0.93 | 0.1 | 25.9 | 0.95 |
| 6 | 0.3 | 17.5 | 0.95 | 0.3 | 14.6 | 0.96 |
| 7 | −0.1 | 20.0 | 0.94 | 0.4 | 18.8 | 0.93 |
| 8 | −0.1 | 15.3 | 0.90 | 0.8 | 20.6 | 0.87 |
| 9 | −0.1 | 20.9 | 0.94 | 0.4 | 24.3 | 0.92 |
| 10 | −0.3 | 18.6 | 0.94 | 0.1 | 22.5 | 0.93 |
| 11 | −0.3 | 17.4 | 0.93 | 0.5 | 17.9 | 0.95 |
| Average | 0.0 | 19.7 | 0.93 | 0.5 | 20.9 | 0.93 |

TABLE 8

| | Training | | | Validation | | |
|---|---|---|---|---|---|---|
| Subject | AD | AAD | rfit | AD | AAD | rfit |
| 1 | −1.2 | 28.5 | 0.86 | 0.4 | 32.8 | 0.85 |
| 2 | 1.1 | 37.8 | 0.90 | 2.7 | 36.4 | 0.87 |
| 3 | 0.7 | 36.3 | 0.84 | 1.2 | 35.2 | 0.79 |
| 4 | −0.1 | 25.2 | 0.73 | −0.9 | 33.0 | 0.74 |
| 5 | −0.2 | 42.1 | 0.82 | 0.4 | 43.8 | 0.85 |
| 6 | 1.3 | 31.9 | 0.85 | 0.5 | 24.6 | 0.88 |
| 7 | −0.3 | 33.8 | 0.84 | 1.0 | 30.6 | 0.85 |
| 8 | −0.1 | 23.6 | 0.76 | 1.5 | 28.5 | 0.78 |
| 9 | −0.5 | 35.2 | 0.85 | 1.5 | 41.5 | 0.8 |
| 10 | −0.5 | 30.3 | 0.85 | 0.7 | 35.9 | 0.84 |
| 11 | −0.8 | 25.3 | 0.86 | 1.0 | 27.4 | 0.89 |
| Average | −0.1 | 31.8 | 0.83 | 0.9 | 33.6 | 0.83 |

The results of the predictive modeling method as outlined in Tables 5-8 indicate very good to excellent outcomes. The models have little to negligible bias as shown by the very low AD values. For the 30-minute predictive models, AAD averages just over 20 mg/dL. For the 60-minute models, the AAD increases about 12 mg/dL. For the 30-minute prediction study, the average $r_{fit}$ is about 0.93, which is excellent, with highs of 0.96. For the 60-minute study, the drop is about 0.1 on the averages to about 0.83. However, there are some with $r_{fit}$ of 0.9 or better.

Example 3

In this Example, a diabetes simulator developed by UVA/Padova, and approved by the FDA, was used to test the present invention. This simulator provides a non-human methodology to test different BGC control algorithms and is considered a valid substitute for animal trials in the early stages for development of an artificial pancreas. This diabetes simulator was used to generate subject data for a comparison of MPC and FBPC with all things being equal except for the differences in the control algorithms. The fitted predictive model used by both methods is the same and predicts G accurately, thus any difference in control performance is due to differences in the control algorithms.

Figure 13:
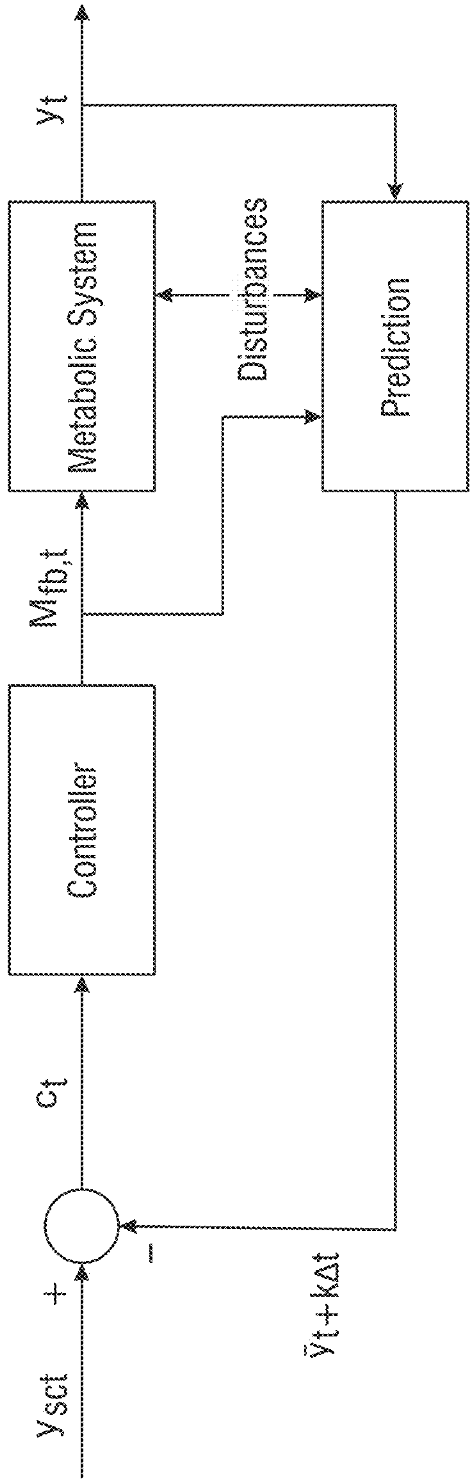
FIG. 13 shows an exemplary FBPC scheme as described herein and based on the glucose monitoring/control system exemplified in FIGS. 2A and 2B.

The FBPC scheme is illustrated in FIG. 13 and is described in FIG. 2. It should be noted that in Example 1 the FBPC method was used in a CSTR system and in this Example the inputs and outputs are specific to controlling BGC by varying insulin flow rate. The present system utilizes a Wiener Model as shown in FIG. 1 and described mathematically in Example 1. In the general context of diabetes, the inputs, $X_i$ for I=1 . . . p, are the measured noninvasive variables such as meal components, physical activity, and emotional stress. The output, y, is BGC. In the diabetes simulator used in this Example, there are no unmeasured disturbances and only two inputs: the amount of carbohydrates in each meal, and IFR.

This Example uses 30 virtual patients, the characteristics of which are summarized in Table 9. To minimize the effect of measurement delay, both the insulin pump and BGC sensor were selected as intravenous (IV) type. As for the scenario tested in this Example, three meals occurred each day at 7 am, 12 pm and 8 pm, and all meals were 50 grams of carbohydrate. To examine the robustness of the proposed FBPC method, a longer than common period of a five-day closed loop control run was utilized. At the start of each trial, a two-day "run-in" period was used to bring the simulator to a consistent day-to-day behavior. Therefore, in total, a seven-day run was used for each subject.

TABLE 9

| Subject | Age | Body Weight (kg) | Fasting BGC (mg/dL) |
|---|---|---|---|
| 1 | 16 | 36.16 | 115 |
| 2 | 18 | 50.88 | 123 |
| 3 | 19 | 54.49 | 127 |
| 4 | 17 | 41.47 | 123 |
| 5 | 19 | 59.34 | 118 |
| 6 | 17 | 52.58 | 119 |
| 7 | 19 | 48.58 | 133 |
| 8 | 16 | 51.79 | 112 |
| 9 | 16 | 67.01 | 120 |
| 10 | 19 | 49.36 | 117 |
| 11 | 3 | 27.79 | 123 |
| 12 | 12 | 32.61 | 124 |
| 13 | 5 | 35.20 | 111 |

TABLE 9-continued

| Subject | Age | Body Weight (kg) | Fasting BGC (mg/dL) |
|---|---|---|---|
| 14 | 5 | 28.32 | 124 |
| 15 | 3 | 36.99 | 121 |
| 16 | 2 | 31.62 | 118 |
| 17 | 2 | 25.48 | 122 |
| 18 | 8 | 28.86 | 123 |
| 19 | 4 | 23.01 | 125 |
| 20 | 7 | 36.15 | 133 |
| 21 | 32 | 79.80 | 122 |
| 22 | 22 | 80.34 | 123 |
| 23 | 42 | 70.87 | 119 |
| 24 | 24 | 67.48 | 119 |
| 25 | 47 | 67.11 | 120 |
| 26 | 23 | 73.01 | 116 |
| 27 | 47 | 46.06 | 115 |
| 28 | 56 | 98.66 | 130 |
| 29 | 24 | 67.78 | 114 |
| 30 | 31 | 80.79 | 113 |

Both control algorithms were supplemented by basal insulin infusion, at the rate of U/hr, that is customized to each of the test subjects as given in Table 9. The set point for each subject was set to their fasting BGC before the start of the trial.

The manipulated input variable, insulin feed rate (IFR), is atypical because it can only decrease BGC. Thus, when a control system calculated the value for bolus insulin to be negative, bolus IFR was necessarily set to zero. In addition, for FBPC, to avoid hypoglycemia, the implemented protocol was to turn bolus IFR off one minute after any meal and then turn it back on one hour before the meal.

A common benchmark used in this area is the percent of values in a range, in this Example, between 70-180 mg/dL as suggested by American Diabetes Association. Values below 70 mg/dL are commonly considered as the hypoglycemic region and above 180 mg/dL is commonly considered as the hyperglycemic region. Thus, the effectiveness a BGC control algorithm is commonly reported by the percentage of time spent in 70-180 mg/dL range. Additionally, other metrics can describe different aspects of the effectiveness such as the spread of BGC about its mean, or its standard deviation (Stdev). In this Example, both metrics are reported.

Three measures of performance are used in this Example for evaluating the fit of the model. The first is the correlation coefficients between the fitted and measured BGC ($r_{fit}$) and given by Eq. (44):

$$r_{fit} = \frac{\sum_{i=1}^{n_t} y_i \hat{y}_i - \frac{\left(\sum_{i=1}^{n_t} y_i\right)\left(\sum_{i=1}^{n} \hat{y}_i\right)}{n_t}}{\sqrt{\sum_{i=1}^{n_t} y_i^2 - \frac{\left(\sum_{i=1}^{n_t} y_i\right)^2}{n_t}} \sqrt{\sum_{i=1}^{n_t} \hat{y}_i^2 - \frac{\left(\sum_{i=1}^{n_t} \hat{y}_i\right)^2}{n_t}}} \quad (44)$$

where $n_t$ is the number of pairs of values in the set, and $y_i$ and $\hat{y}_i$ are the $i^{th}$ measured and fitted values in the set, respectively. The closer this statistic is to 1.0, the better the model fits the measured data without consideration of model bias. The second statistic is the averaged error (AE), which gives a measure of model bias. As shown in the equation below, it is the average of $y_i - \hat{y}_i$.

$$AE = \frac{1}{n_t} \sum_{i=1}^{n_t} (y_i - \hat{y}_i) \quad (45)$$

The final statistic is the averaged absolute error (AAE), which is a measure of the average closeness of $y_i$ to $\hat{y}_i$, as shown in Eq. (46).

$$AAE = \frac{1}{n_t} \sum_{i=1}^{n_t} |y_i - \hat{y}_i| \quad (46)$$

Figure 10:
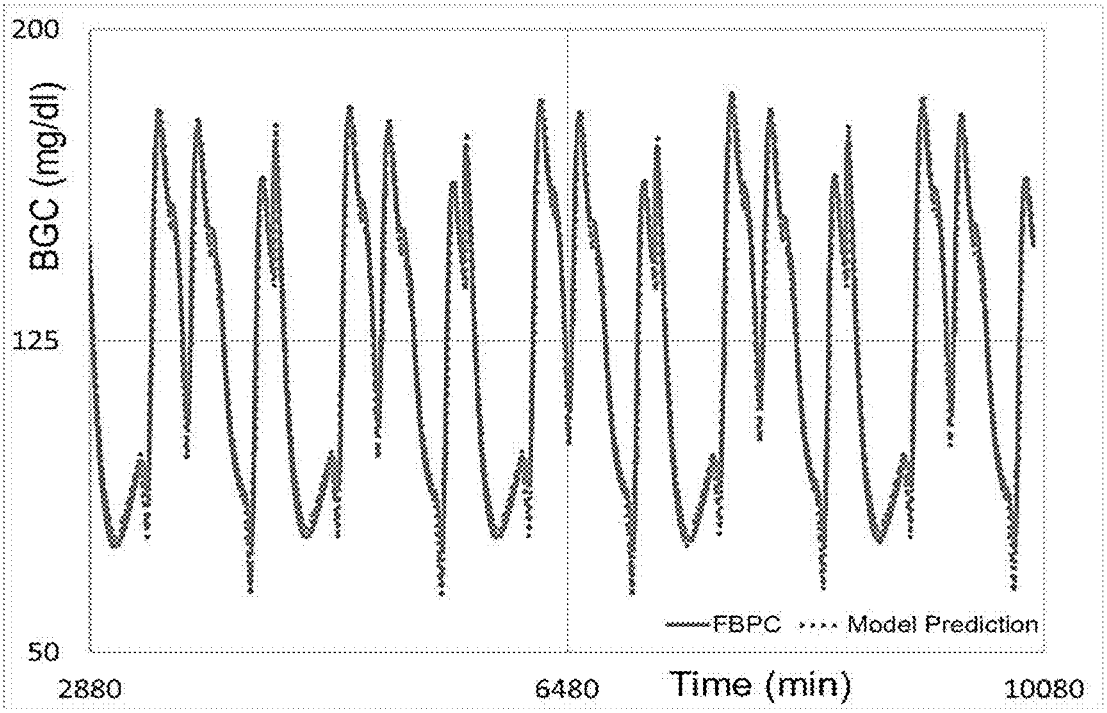
FIG. 10 shows a comparison of the FBPC and MPC for BGC control n steps into the future from Example 3.
Figure 11A:
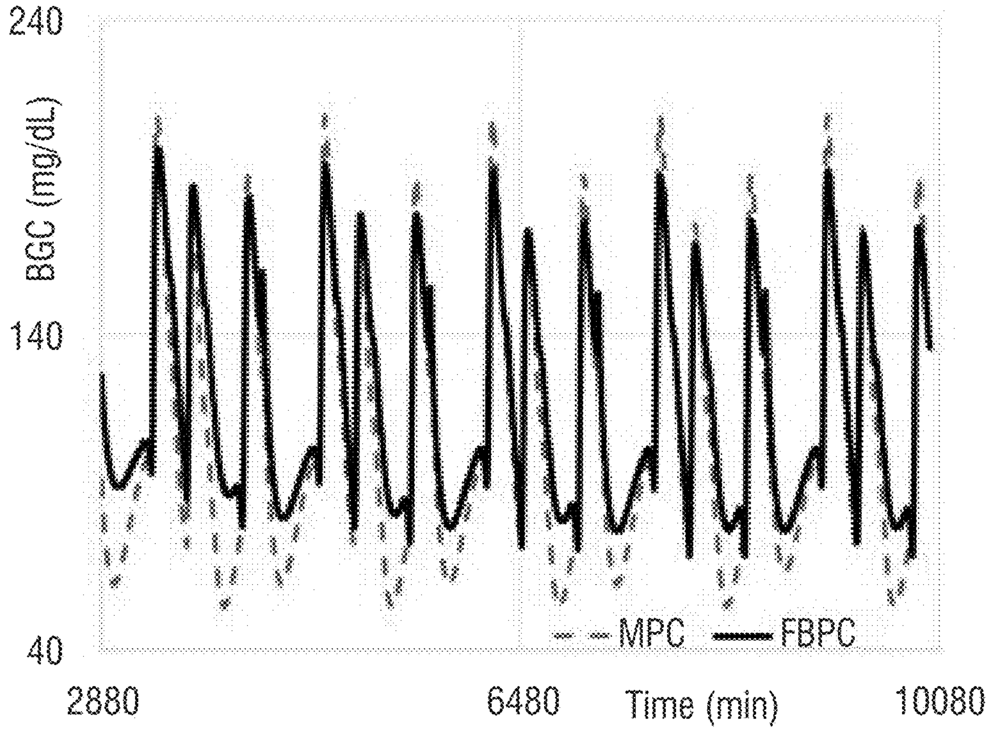
FIGS. 11A-11E show the graphical control run results for both the MPC and FBPC for the first five (5) test subjects.
Figure 11B:
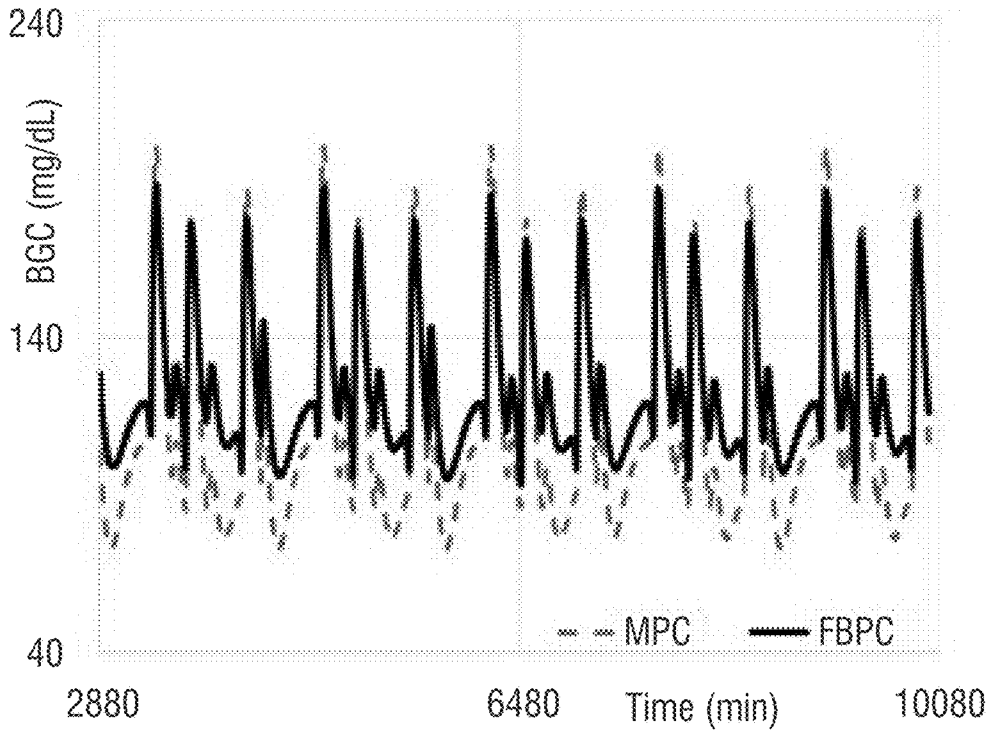
Figure 11C:
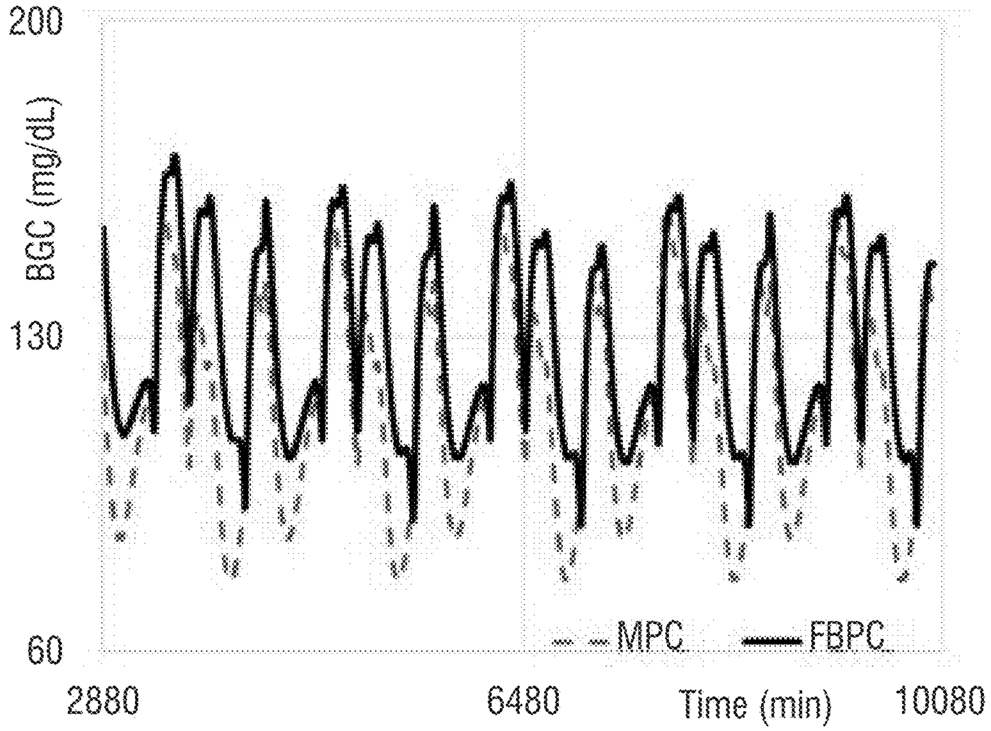
Figure 11D:
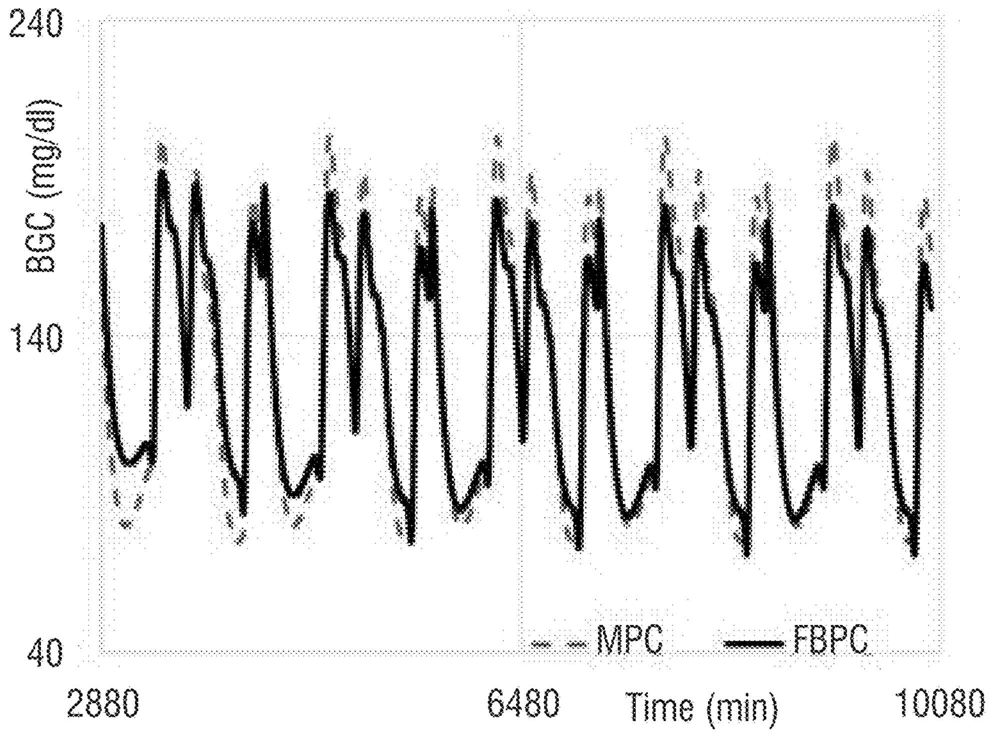
Figure 11E:
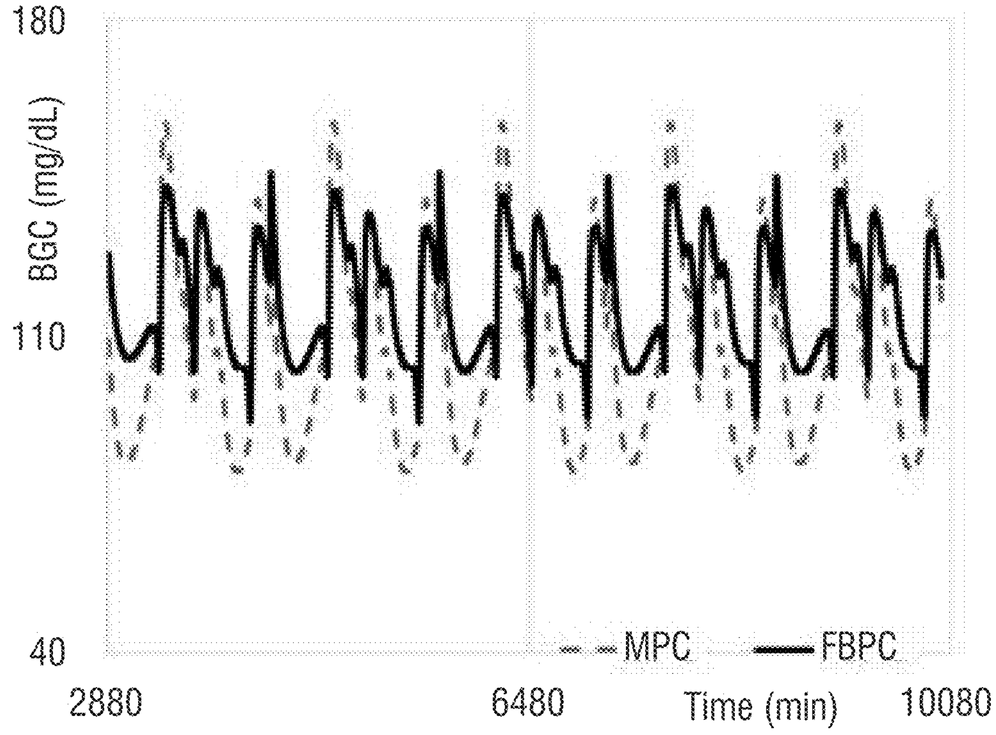

Model development followed the cross-validation protocol of Example 1 as described in Eq. (30). The size and type of data sets for model identification are the same as in Eq. (26). The controllers were tuned to give the tightest control of glucose levels. Table 10 gives a summary of the modeling results in this Example for each subject. As shown, $r_{fit}$ is at, or nearly at, its maximum value of one (1) for all 30 subjects. Similarly, the AE and AAE results are also excellent averaging 0.22 and 1.7 mg/dL, respectively. To demonstrate the excellent accuracy of the model n time steps into the future under automatic control, results are shown in FIG. 10 for Subject 4 with $r_{fit}$=0.99, AE=0.068, and AAE=1.897.

FIGS. 11A-E show graphical control run results for both algorithms (MPC and FBPC) for the first five (5) subjects and FIGS. 12A-E show insulin feed rates (IFR) for these subjects during the control runs. The control run results for all the subjects are outlined in Tables 11A and 11B. Table 12 gives the tuning parameters for the first five (5) subjects.

TABLE 10

| | $r_{fit}$ | | | AE (mg/dL) | AAE (mg/dL) | $\tau_1$ Carb | $\tau_2$ Insulin |
|---|---|---|---|---|---|---|---|
| Subject | Training | Validation | Testing | Testing | Testing | (mm) | (min) |
| 1 | 0.999 | 0.999 | 0.999 | 0.275 | 1.694 | 574.9 | 804.4 |
| 2 | 0.997 | 0.996 | 0.997 | 0.433 | 2.161 | 654.9 | 916.5 |
| 3 | 0.999 | 0.999 | 0.999 | 0.219 | 1.218 | 669.0 | 871.5 |
| 4 | 0.999 | 0.999 | 0.999 | 0.068 | 1.897 | 796.8 | 1131.9 |
| 5 | 1.000 | 0.999 | 0.999 | 0.088 | 1.454 | 1015.6 | 1078.1 |
| 6 | 0.999 | 0.999 | 1.000 | 0.271 | 0.916 | 715.3 | 1145.6 |
| 7 | 1.000 | 1.000 | 1.000 | 0.123 | 1.110 | 571.0 | 1078.4 |
| 8 | 0.999 | 0.999 | 0.999 | 0.510 | 1.502 | 813.8 | 800.0 |
| 9 | 0.999 | 0.999 | 0.999 | 0.226 | 1.456 | 851.0 | 1048.9 |
| 10 | 0.998 | 0.997 | 0.998 | 0.242 | 1.692 | 864.5 | 1112.7 |
| 11 | 0.999 | 0.999 | 0.999 | 0.878 | 2.890 | 736.1 | 818.0 |
| 12 | 0.999 | 0.999 | 0.999 | 0.589 | 2.243 | 613.1 | 879.6 |
| 13 | 0.999 | 0.999 | 0.999 | 0.574 | 2.361 | 723.3 | 943.4 |

TABLE 10-continued

| Subject | $r_{fit}$ Training | $r_{fit}$ Validation | $r_{fit}$ Testing | AE (mg/dL) Testing | AAE (mg/dL) Testing | $\tau_1$ Carb (mm) | $\tau_2$ Insulin (min) |
|---|---|---|---|---|---|---|---|
| 14 | 0.999 | 0.999 | 0.999 | 1.790 | 4.066 | 905.6 | 994.6 |
| 15 | 0.996 | 0.995 | 0.997 | 0.437 | 3.335 | 540.7 | 772.5 |
| 16 | 0.998 | 0.998 | 0.999 | 0.616 | 3.359 | 680.2 | 814.9 |
| 17 | 0.998 | 0.998 | 0.999 | 1.446 | 5.032 | 782.8 | 806.2 |
| 18 | 0.998 | 0.998 | 0.999 | 0.426 | 3.532 | 822.4 | 1032.4 |
| 19 | 0.999 | 0.999 | 0.999 | 1.416 | 3.982 | 927.8 | 914.8 |
| 20 | 0.999 | 0.998 | 0.999 | 0.625 | 2.422 | 779.0 | 916.3 |
| 21 | 0.997 | 0.997 | 0.998 | 0.129 | 1.271 | 630.7 | 821.2 |
| 22 | 0.996 | 0.996 | 0.997 | 0.043 | 0.871 | 447.9 | 578.2 |
| 23 | 0.999 | 0.999 | 0.999 | 0.231 | 1.061 | 779.0 | 883.6 |
| 24 | 0.999 | 0.998 | 0.999 | 0.093 | 1.076 | 681.8 | 1053.9 |
| 25 | 0.999 | 0.999 | 0.999 | 0.148 | 1.190 | 798.9 | 1063.5 |
| 26 | 0.998 | 0.997 | 0.998 | 0.049 | 1.151 | 480.0 | 800.0 |
| 27 | 0.999 | 0.999 | 0.999 | 0.705 | 2.319 | 867.2 | 1045.1 |
| 28 | 0.998 | 0.998 | 0.998 | 0.264 | 1.521 | 664.9 | 902.8 |
| 29 | 0.999 | 0.998 | 0.999 | 0.115 | 1.138 | 549.5 | 813.2 |
| 30 | 0.998 | 0.997 | 0.998 | 0.111 | 1.028 | 580.8 | 780.0 |
| Mean | 0.999 | 0.998 | 0.999 | 0.438 | 2.032 | 717.3 | 920.7 |

TABLE 11A

| | | FBPC | | | MPC | | |
|---|---|---|---|---|---|---|---|
| Subject | Set Point | Mean (mg/dL) | Stdev (mg/dL) | 70-180 mg/dL (%) | Mean (mg/dL) | Stdev (mg/dL) | 70-180 mg/dL (%) |
| 1 | 115 | 117.9 | 34.2 | 94.7 | 108.2 | 42.4 | 69.8 |
| 2 | 123 | 123.4 | 22.5 | 97.8 | 110.8 | 32.7 | 94.2 |
| 3 | 127 | 127.3 | 20.6 | 100.0 | 114.8 | 23.6 | 100.0 |
| 4 | 123 | 128.1 | 33.4 | 96.0 | 130.0 | 41.3 | 84.2 |
| 5 | 118 | 118.1 | 13.1 | 100.0 | 108.1 | 21.9 | 100.0 |
| 6 | 119 | 119.4 | 20.8 | 100.0 | 106.9 | 25.5 | 100.0 |
| 7 | 133 | 134.4 | 42.3 | 78.0 | 104.3 | 48.0 | 60.7 |
| 8 | 112 | 112.0 | 20.6 | 99.9 | 103.1 | 24.9 | 93.8 |
| 9 | 120 | 119.9 | 17.4 | 100.0 | 115.5 | 23.0 | 100.0 |
| 10 | 117 | 116.9 | 16.6 | 100.0 | 109.3 | 25.6 | 98.7 |
| 11 | 123 | 123.1 | 35.0 | 92.4 | 121.9 | 39.0 | 87.6 |
| 12 | 124 | 125.9 | 40.6 | 83.7 | 112.2 | 47.9 | 65.6 |
| 13 | 111 | 127.4 | 29.4 | 96.1 | 107.2 | 33.5 | 85.0 |
| 14 | 124 | 123.7 | 22.2 | 97.7 | 105.9 | 28.7 | 89.0 |
| 15 | 121 | 121.6 | 32.9 | 93.6 | 117.9 | 41.9 | 78.7 |
| 16 | 118 | 120.7 | 21.0 | 100.0 | 123.2 | 34.8 | 88.5 |
| 17 | 122 | 122.6 | 26.5 | 93.0 | 126.9 | 29.6 | 91.8 |
| 18 | 123 | 122.0 | 36.1 | 92.1 | 97.9 | 40.8 | 65.0 |
| 19 | 125 | 124.8 | 13.7 | 100.0 | 120.8 | 17.9 | 100.0 |
| 20 | 133 | 133.1 | 20.4 | 98.4 | 123.8 | 26.7 | 97.0 |
| 21 | 122 | 122.0 | 13.4 | 100.0 | 121.6 | 19.1 | 100.0 |
| 22 | 123 | 123.6 | 9.6 | 100.0 | 123.5 | 15.9 | 100.0 |
| 23 | 119 | 121.5 | 11.1 | 99.6 | 119.9 | 15.8 | 99.7 |
| 24 | 119 | 119.1 | 14.1 | 100.0 | 115.7 | 18.6 | 100.0 |
| 25 | 120 | 120.0 | 11.9 | 100.0 | 120.6 | 16.4 | 100.0 |
| 26 | 116 | 121.1 | 16.9 | 100.0 | 121.4 | 24.2 | 99.1 |
| 27 | 115 | 115.0 | 14.3 | 100.0 | 112.1 | 22.5 | 100.0 |
| 28 | 130 | 130.0 | 14.5 | 100.0 | 128.3 | 19.5 | 100.0 |
| 29 | 114 | 112.9 | 15.5 | 100.0 | 113.5 | 22.1 | 100.0 |
| 30 | 113 | 112.7 | 13.5 | 100.0 | 109.0 | 16.2 | 100.0 |
| Average | | 122.0 | 21.8 | 97.1 | 115.1 | 28.0 | 91.6 |

TABLE 11B

| Subject | Set Point | MPC Stdev > FBPC Stdev (%) | MPC Stdev − FBPC Stdev (mg/dL) |
|---|---|---|---|
| 1 | 115 | 24.0 | 8.2 |
| 2 | 123 | 45.3 | 10.2 |
| 3 | 127 | 14.6 | 3.0 |

TABLE 11B-continued

| Subject | Set Point | MPC Stdev > FBPC Stdev (%) | MPC Stdev − FBPC Stdev (mg/dL) |
|---|---|---|---|
| 4 | 123 | 23.7 | 7.9 |
| 5 | 118 | 67.2 | 8.8 |
| 6 | 119 | 22.6 | 4.7 |
| 7 | 133 | 13.5 | 5.7 |
| 8 | 112 | 20.9 | 4.3 |
| 9 | 120 | 32.2 | 5.6 |
| 10 | 117 | 54.2 | 9.0 |
| 11 | 123 | 11.4 | 4.0 |
| 12 | 124 | 18.0 | 7.3 |
| 13 | 111 | 13.9 | 4.1 |
| 14 | 124 | 29.3 | 6.5 |
| 15 | 121 | 27.4 | 9.0 |
| 16 | 118 | 65.7 | 13.8 |
| 17 | 122 | 11.7 | 3.1 |
| 18 | 123 | 13.0 | 4.7 |
| 19 | 125 | 30.7 | 4.2 |
| 20 | 133 | 30.9 | 6.3 |
| 21 | 122 | 42.5 | 5.7 |
| 22 | 123 | 65.6 | 6.3 |
| 23 | 119 | 42.3 | 4.7 |
| 24 | 119 | 31.9 | 4.5 |
| 25 | 120 | 37.8 | 4.5 |
| 26 | 116 | 43.2 | 7.3 |
| 27 | 115 | 57.3 | 8.2 |
| 28 | 130 | 34.5 | 5.0 |
| 29 | 114 | 42.6 | 6.6 |
| 30 | 113 | 20.0 | 2.7 |
| Average | | 32.9 | 6.2 |

TABLE 12

| | FBPC | | | | MPC | |
|---|---|---|---|---|---|---|
| Subject | $K_c$ | $\tau_I$ (min) | $\tau_D$ (min$^{-1}$) | Total Insulin (U) | J | Total Insulin (U) |
| 1 | −0.00004 | 100 | 600 | 59.3 | 600 | 75.3 |
| 2 | −0.00004 | 50 | 600 | 77.6 | 350 | 94.2 |
| 3 | −0.00006 | 100 | 300 | 44.7 | 400 | 57.8 |
| 4 | −0.00005 | 90 | 450 | 115.5 | 600 | 128.1 |
| 5 | −0.00006 | 100 | 500 | 94.9 | 250 | 113.7 |

As outlined in Tables 11A and 11B, and as illustrated in FIGS. 11A-E, the control run results of FBPC are considerately better than MPC. In FIGS. 11A-E, FBPC has tighter variation of BGC than MPC in all cases, and much better in some cases (e.g., Subject 5). As given in Tables 11A and 11B, FBPC has smaller Stdev and larger % in the 70-180 mg/dL range, except when both give 100%, than MPC in all 30 cases. Relative to the Stdev of FBPC, the % difference of MPC is as high as 67.2%, greater than 40% for 10 of the 30 subjects, and has an average value of nearly 33% higher. In absolute magnitude, the Stdev of MPC is greater than FBPC; as high as 13.8 mg/dL, greater than 7 mg/dL for 10 subjects, and has an average value of 6.2 mg/dL.

Table 12 gives the values of the tuning parameters for only the first five subjects for space consideration. The values for FBPC are surprising very similar, which may assist greatly in obtaining tuning parameters for FBPC. The values of the one tuning parameter for MPC, J, range from 250 to 600. These values, and the spread between them, are considerably large. The large values are not surprising when considering the large values of the lags shown in Table 10; $\tau_i$ values for carbohydrates and IFR have averages of 717.3 min. and 920.7 min., respectively.

Figure 12A:
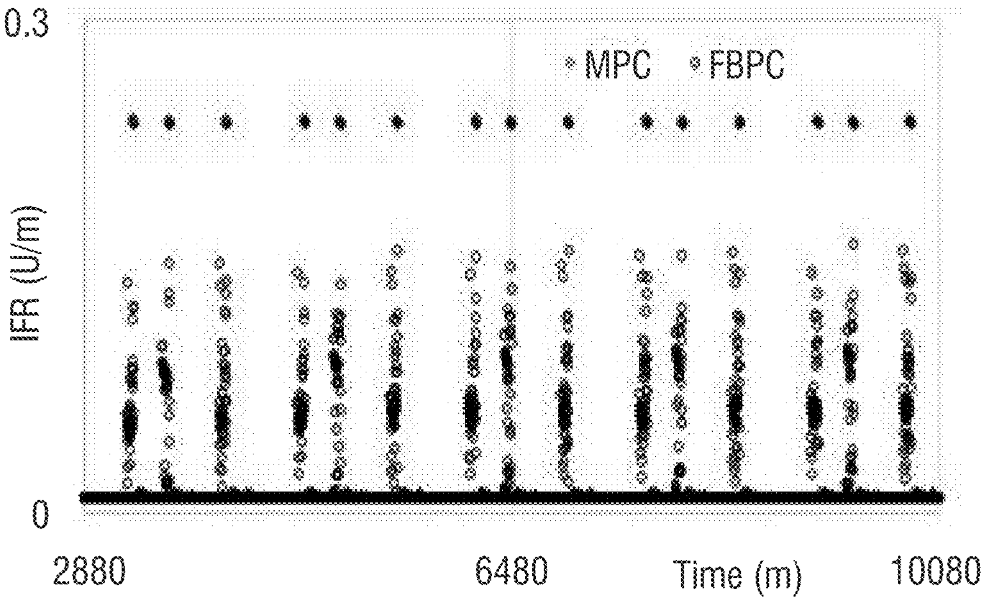
FIGS. 12A-12E show the bolus profiles of the insulin feed rates for the first five (5) test subjects both under an MPC and FBPC.
Figure 12B:
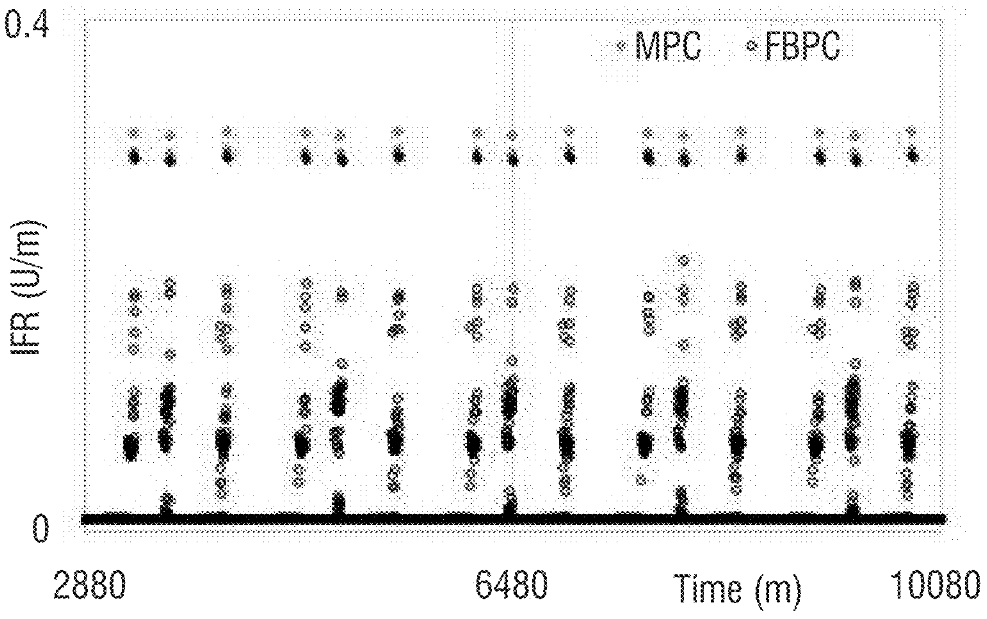
Figure 12C:
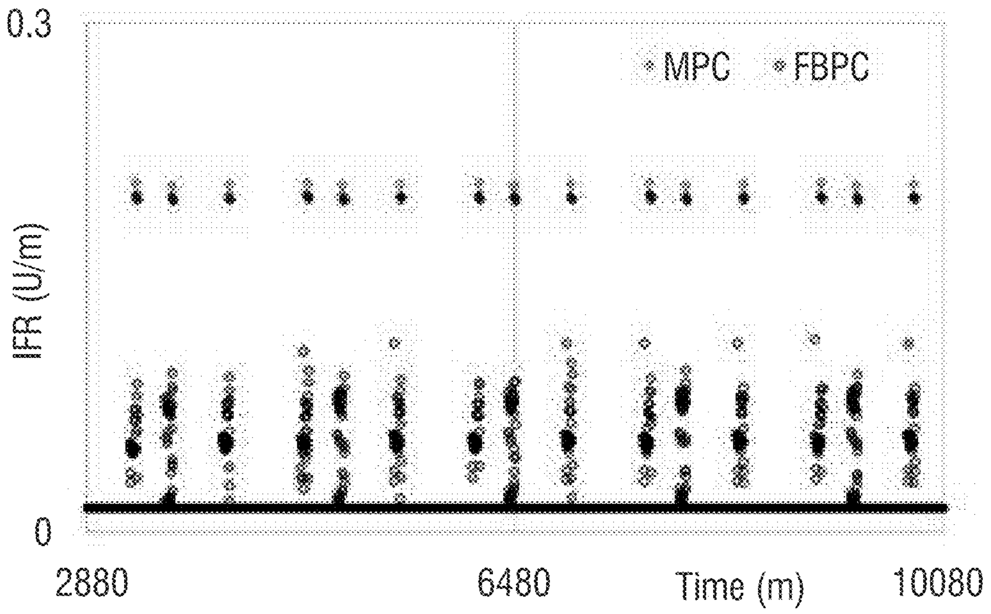
Figure 12D:
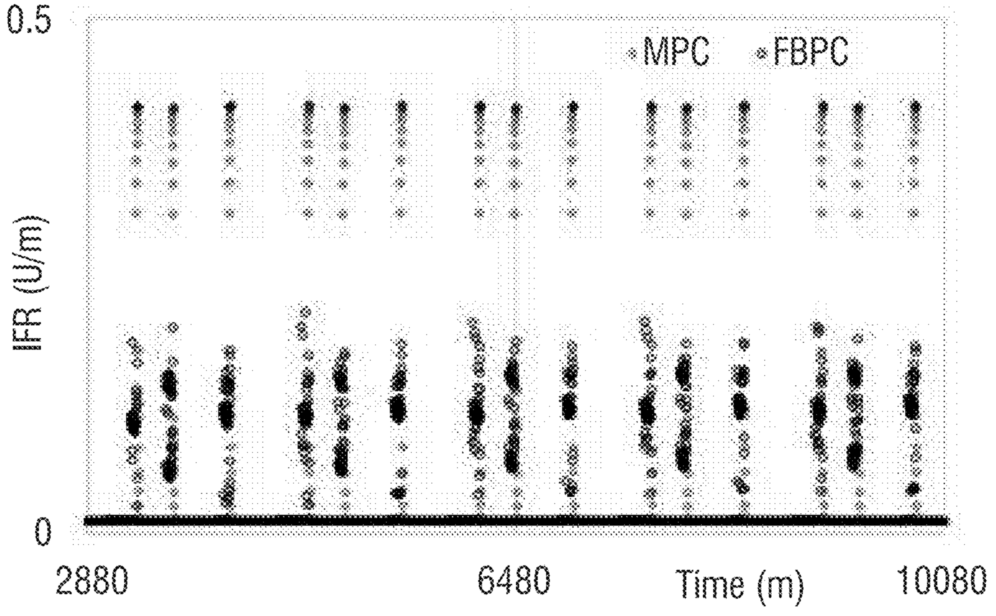
Figure 12E:
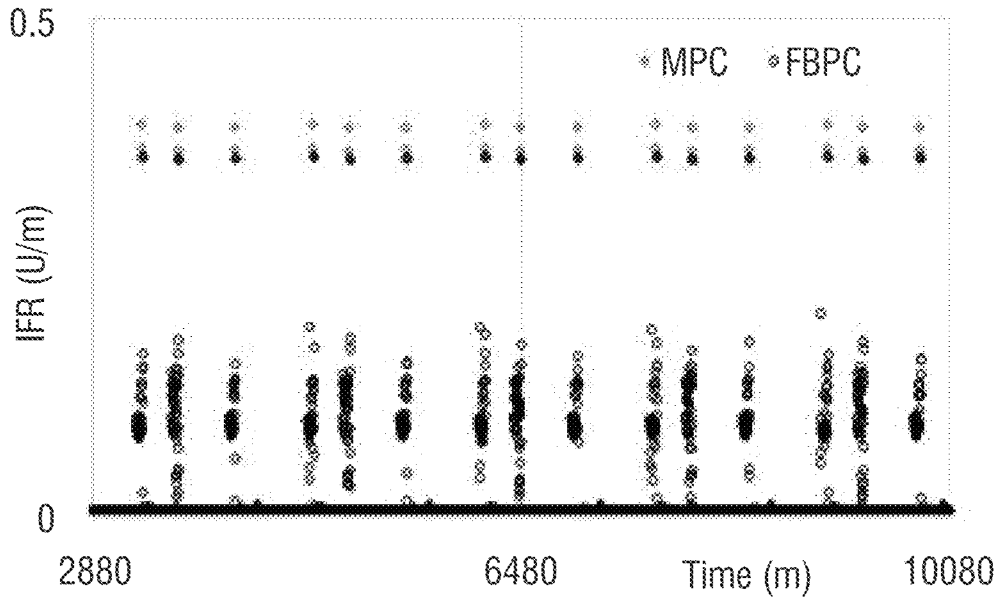
Figure 12F:
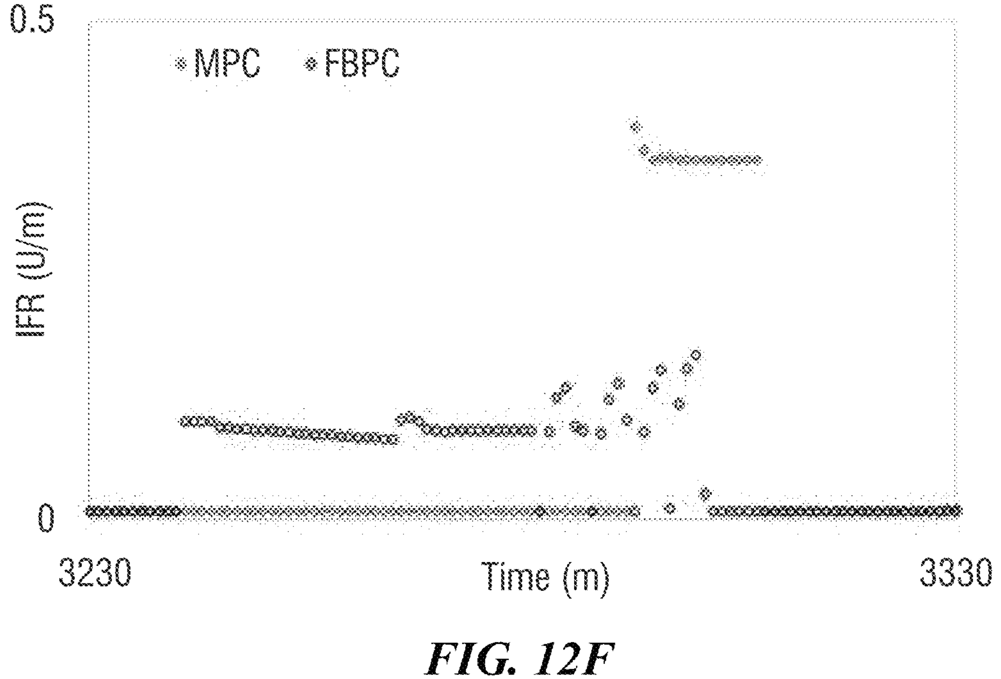
FIG. 12F shows the insulin feed rate of one meal in detail for test subject 5.

Table 12 shows the amount of total bolus insulin infused during the control runs of five days. In each case, this amount is significantly higher for MPC. The bolus profiles over time for these five subjects can be seen in FIGS. 12A-E. As shown, for FPBC, the pulses of bolus insulin are more frequent and much smaller than MPC in all cases. For Subject 5, FIG. 12F shows one meal in greater detail. As illustrated, bolus injection for FBPC covers a wider time-frame, is fairly uniform, and its values are considerably lower than MPC, which is also fairly uniform, but less frequent.

Therefore, methods and systems have been described relating to insulin delivery. It should be understood that the present invention contemplates numerous variations, options, and alternatives. For example, where sensed information is provided as input, the sensed information may be supplied from any number of sensors including sensors associated with wearable devices, mobile devices, or other computing devices. Where information is input by users, it is to be understood that the information may be input using wearable devices, mobile devices, or other computing devices including the same device used for insulin delivery. It is further to be understood that the model may be stored on any number of computing devices including a mobile device, or the same device used for insulin delivery.

The above specification provides a description of the manufacture and use of the disclosed compositions and methods. Since many embodiments can be made without departing from the spirit and scope of the invention, the invention resides in the claims.

What is claimed is:

1. A wearable device for administering insulin, the wearable device comprising:

an apparatus for administering insulin;

a sensor;

the wearable device in operable communication with a PID controller comprising a feedback predictive control stored on a machine readable non-transitory media associated with a computing device, the computing device in operable communication with the sensor; wherein the feedback predictive control comprises a first model and a second model; wherein the first model is a predictive model; and wherein the second model is a noise model, which models unmeasured disturbances and bias;

wherein the machine readable non-transitory media is capable of receiving predictive inputs and measured inputs and wherein said predictive inputs and/or measured inputs are parametrized by the first model to provide an output, wherein the output is provided to the second model and to the PID controller, wherein the PID controller controls an insulin flow rate, and wherein the second model provides feedback to the PID controller.

2. The wearable device of claim 1, wherein the wearable device comprises a wireless transceiver.

3. The wearable device of claim 2, wherein the wireless transceiver is in communication with the computing device or a mobile device; and wherein the computing device is in wireless operable communication with the sensor.

4. The wearable device of claim 3, wherein the mobile device can receive one or more inputs provided manually by a user.

5. The wearable device of claim 4, wherein one or more inputs provided manually by the user include at least one of the following: consumed energy, basal insulin, or bolus insulin.

6. The wearable device of claim 1, further comprising a monitoring system, wherein at least one of said measured inputs are provided by the monitoring system.

7. The wearable device of claim 6, wherein the monitoring system monitors at least one of the following variables: body position, movement, heat dissipated, skin temperature, near body temperature, galvanic skin response, and sleep, basal insulin, or bolus insulin.

8. The wearable device of claim 1, wherein the sensor comprises at least one of the following: a soft sensor, a remote sensor, an accelerometer, or a thermistor.

9. The wearable device of claim 1, wherein the first model is:

$$f(V) = n_t + \varepsilon_t = a_0 + V_{FI,t} + a_{A1} v_{A_{l,t}} + \ldots + a_{Ap} v_{A_p,t}$$

and wherein the second model is $$\hat{y}_{t+k\Delta t} = \hat{n}_{t+k\Delta t} + \hat{\varphi}_1 (y_t - \hat{n}_t) + \hat{\varphi}_2 (\hat{y}_{t-\Delta t} - \hat{n}_{t-\Delta t}) + \\ = \hat{n}_{t+k\Delta t} + \hat{\varphi}_1 e_t + \hat{\varphi}_2 e_{t-\Delta t} +$$

wherein $e_t$ is a residual at t of the first model, and subject to: subject to $$\sum_{i=1}^{4} \varphi_1 = 1.$$

10. The wearable device of claim 1, wherein the apparatus for administering insulin is an automatic insulin pump, a remotely controlled insulin pump, an IV, a catheter, or an artificial pancreas.

11. A method of administering insulin via the wearable device of claim 1 comprising steps of:

determining an amount of insulin to administer using a feedback predictive control, wherein the feedback predictive control is stored on the machine readable non-transitory media;

providing predictive inputs and measured inputs to the first model;

using the predictive inputs and the measured inputs to provide a parametrized first model to provide the output, wherein the output is provided to the second model and to the PID controller;

providing feedback to the PID controller from the second model;

administering insulin using the apparatus for administering insulin based on the output and the feedback, wherein the administration of insulin is adjusted to nullify the effect of any disturbances on blood glucose concentration based on a predicted blood glucose value.

12. The method of claim 11, wherein one or more of said measured inputs are provided by an automatic monitoring system.

13. The method of claim 12, wherein the automatic monitoring system comprises one or more sensors comprising at least one of the following; a soft sensor, a remote sensor, an accelerometer, or a thermistor.

14. The method of claim 12, wherein the automatic monitoring system monitors at least one of the following variables; body position, movement, heat dissipated, skin temperature, near body temperature, galvanic skin response, and sleep, basal insulin, or bolus insulin.

15. The method of claim 11, wherein one or more of said predictive inputs are provided manually by a user.

16. The method of claim 11, wherein the wearable device comprises a wireless transceiver.

17. The method of claim 16, wherein the wireless transceiver is in communication with the computing device or a mobile device.

18. The method of claim 17, wherein the mobile device can receive one or more inputs provided manually by a user; and wherein the user manually provides one or more inputs comprising at least one of the following: consumed energy, basal insulin, or bolus insulin.

19. The method of claim 11, wherein the first model is:

$$f(V) = n_t + \varepsilon_t = a_0 + V_{FI,t} + a_{A1} v_{A_{l,t}} + \ldots + a_{Ap} v_{A_p,t}$$

and wherein the second model is $$\begin{aligned}\hat{y}_{t+k\Delta t} &= \hat{n}_{t+k\Delta t} + \hat{\varphi}_1 (y_t - \hat{n}_t) + \hat{\varphi}_2 (\hat{y}_{t-\Delta t} - \hat{n}_{t-\Delta t}) + \\ &= \hat{n}_{t+k\Delta t} + \hat{\varphi}_1 e_t + \hat{\varphi}_2 e_{t-\Delta t} +\end{aligned}$$

wherein $e_t$ is a residual at t of the first model, and subject to: subject to $$\sum_{i=1}^{4} \varphi_1 = 1.$$

20. The method of claim 11, wherein the apparatus for administering insulin is an automatic insulin pump, a remotely controlled insulin pump, an IV, a catheter, or an artificial pancreas.

* * * * *